(12) United States Patent
Crow et al.

(10) Patent No.: US 6,372,727 B1
(45) Date of Patent: Apr. 16, 2002

(54) METALLOPORPHYRIN TREATMENT OF NEUROLOGIC DISEASE

(75) Inventors: John P. Crow; Alvaro G. Estevez, both of Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/687,275

(22) Filed: Oct. 13, 2000

Related U.S. Application Data

(60) Provisional application No. 60/159,273, filed on Oct. 13, 1999, now abandoned.

(51) Int. Cl.⁷ .................. A61K 31/409; A61K 31/675; C07D 487/22; C07F 9/572
(52) U.S. Cl. .................. 514/81; 514/185; 540/145
(58) Field of Search .................. 514/81, 185; 540/145

(56) References Cited

U.S. PATENT DOCUMENTS 5,262,532 A  11/1993  Tweedle .................. 487/22

OTHER PUBLICATIONS

Bettelheim et al J. Electroanal. Chem. Interfacial Electrochem. 266(1) (1989) 93–108 (CAS abstract only).*
Guo et al Gaodeng Jiaoyu Chubanshe 18(2) (1997) 242–246 (CAS abstract only).*
Harada et al Inorg. Chem. 36 (1997) 6099–6102.*
Yoshimura Bull Chem. Soc. Jpn. 64 (1991) 2819–2828.*
Al–Chalabi et al Curr. Opin. Neurol. 13(4) (2000) 397–405 (Medline abstract only).*
Hurko et al J. Neuro. Sci. 180 (2000) 21–28.*
Rowland J. Neuro. Sci. 180 (2000) 2–6.*
Storch et al J. Neurochem. 75(6) (2000) 2259–2269 (Medline abstract only).*

* cited by examiner

*Primary Examiner*—Richard L. Raymond
(74) *Attorney, Agent, or Firm*—Benjamin Aaron Adler

(57) ABSTRACT

The present invention provides a method of treating amyotrophic lateral sclerosis and other neurologic diseases by administering a compound of the formula

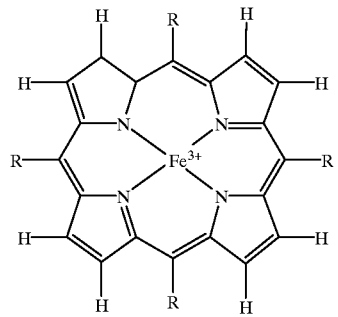

where R is selected from the group consisting of $(C_6H_4)CO_2H$, $(C_6H_4)CO_2CH_3$, $(C_6H_4)(3,5\text{-}OH)_2$, $(C_6H_4)CH_2OH$, $(C_6H_4)OCH_3$, $(C_6H_4)PO_3H$, $(C_6H_4)SO_3H$, $(C_6H_4)(3\text{-}NO_2\text{-}4\text{-}OH)$, $(C_6H_4)NO_2$, $(C_6H_4)OPO_3H$, $(C_6H_4)OSO_3H$, $(C_6H_4)CH_2CO_2H$, $(C_6H_4)NH_2$, and $(C_6H_4)CONH_2$. Also provided is a method for preserving donor organs using a solution comprising the instant compounds.

14 Claims, 15 Drawing Sheets

| Name | Metal |
|---|---|
| MnPPIX | $Mn^{+3}$ |
| FePPIX | $Fe^{+3}$ |

| Name | Metal | R |
|---|---|---|
| MnTMPyP | $Mn^{+3}$ | R1 |
| FeTMPyP | $Fe^{+3}$ | R1 |
| CuTMPyP | $Cu^{+2}$ | R1 |
| FeTSPP | $Fe^{+3}$ | R2 |
| CuTSPP | $Cu^{+2}$ | R2 |
| MnTBAP | $Mn^{+3}$ | R3 |
| ZnTBAP | $Zn^{+2}$ | R3 |
| PtTMPyP | $Pt^{+2}$ | R3 |
| PdTBAP | $Pd^{+2}$ | R3 |

Fig. 1

FeTCPP      R1

FeTMeO-TCPP      R2

METALLOPORPHYRIN TREATMENT OF NEUROLOGIC DISEASE

CROSS-REFERENCE TO RELATED APPLICATIONS

This application claims benefit of priority of provisional application U.S. Serial No. 60/159,273, filed Oct. 13, 1999, now abandoned.

FEDERAL FUNDING LEGEND

The present invention was created in part using federal funds under NIH grant NS35871-03. Accordingly, the U.S. government has certain rights in this invention.

BACKGROUND OF THE INVENTION

1. Field of the Invention

The present invention relates generally to the fields of biochemistry and pharmacology. More specifically, the present invention relates to a treatment of neurologic diseases such as amyotrophic lateral sclerosis using compounds such as metalloporphyrins or derivatives thereof.

2. Description of the Related Art

The low molecular weight metalloporphyrins (MPs) comprise a general class of compounds that contain a tetra-coordinated metal atom and various cationic, anionic, or uncharged functional groups extending outward from the planar porphyrin ring (FIG. 1). Many compounds in this class possess four identical functional groups making the molecule symmetrical. The nature of the functional groups can dramatically alter the redox behavior of the transition metal-containing porphyrins (1).

The manganese-containing porphyrins are perhaps the most extensively studied, largely because of the ability of some Mn-porphyrins to undergo cyclic one-electron oxidation and reduction under physiological conditions and thereby mimic some of the enzymatic properties of superoxide dismutases (2–5). Other catalytic activities of the Mn-porphyrins have been described, including the ability to decompose hydrogen peroxide (6) and peroxynitrite (7–9). Mammalian cells eliminate hydrogen peroxide primarily via the actions of catalase and glutathione peroxidase and scavenge superoxide with two copper, zinc-containing superoxide dismutases and one manganese-containing form. Glutathione peroxidase, in the presence of glutathione, has been shown to b e capable of catalytically decomposing peroxynitrite (10), raising the possibility that glutathione peroxidase or other selenoproteins may serve as natural peroxynitrite scavengers. However, protein tyrosine nitration occurs even under physiological conditions (and increases dramatically in pathologic states) indicating that at least some peroxynitrite escapes whatever endogenous detoxification systems may exist (11). Thus, compounds with the potential to catalytically decompose or otherwise scavenge peroxynitrite hold great promise as therapeutic agents in a number of disease conditions (11).

The ability of transition metal-containing metalloporphyrins to protect against peroxynitrite-mediated injury in vivo depends primarily on three properties: 1) how fast the metalloporphyrins react with peroxynitrite anion, i.e., how well they channel it into a metalloporphyrin-mediated reaction pathway, 2) how fast, and under what conditions the metalloporphyrins recycle to the reduced starting compounds, and 3) how well the metalloporphyrins contain or quench the resulting reactive intermediates. The rate constants for simple bimolecular reactions of some Mn- (8,12,13) and Fe-porphyrins (7) with peroxynitrite exceed $10^6$ $M^{-1}s^{-1}$, suggesting that they can potentially compete with many biomolecular targets which are known to react more slowly. Manganese porphyrins are capable of catalytically decomposing peroxynitrite in the presence of reductants like ascorbate or Trolox (8,12,13). At least one iron-porphyrin, iron(III)-meso-tetra-(N-methyl-4-pyridyl)-porphine chloride (FeTMPyP) has been shown to catalytically decompose peroxynitrite in the absence of added reductants, suggesting that re-reduction of the intermediate Fe(IV) form was not rate-limiting (7); this is explained, in part, by the recent work of Lee et al. (14) which indicates that peroxynitrite can also be decomposed by the intermediate Fe(IV) form of FeTMPyP. However, the ability of either Mn- or Fe-porphyrins to contain or quench reactive intermediates has not been rigorously examined and the precise mechanisms by which Mn and Fe porphyrins protect against oxidant-mediated injury in vivo have not been established.

The prior art is deficient in the lack of effective iron(III) porphyrins and their derivatives and analogs as a means of treating neurologic diseases such as amyotrophic lateral sclerosis (ALS). The present invention fulfills this long-standing need and desire in the art.

SUMMARY OF THE INVENTION

The present invention shows that there is abundant evidence for oxidant-mediated injury to motor neurons in ALS and a strong rationale for use of novel antioxidant compounds like the metalloporphyrins. In one embodiment of the present invention, there is provided a compound of the formula

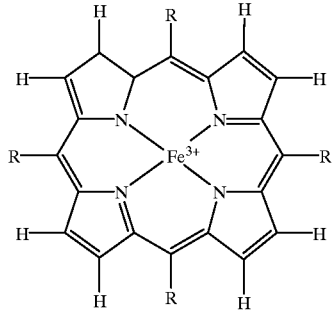

where R is selected from the group consisting of $PhCO_2CH_3$, $Ph(3,5-OH)_2$, $PhCH_2OH$, $PhOCH_3$, $PhPO_3^{-2}$, $Ph(3-NO_2-4-OH)$, $PhNO_2^{-}$, $PhOPO_3^{-2}$, $PhOSO_3^{-2}$, $PhCH_2CO_2^{-}$, $PhNH_2$, and $PhCONH_2$. In another embodiment of the present invention, there is provided a pharmaceutical composition, comprising these compounds and additional compounds where R also may be $PhCO_2^{-}$ and $PhSO_3^{-}$ and a pharmaceutically acceptable carrier.

In another embodiment of the present invention, there is provided a method of treating an individual with Amyotrophic Lateral Sclerosis in need of such treatment comprising the step of administering to the individual a pharmacologically effective dose of the instant pharmaceutical compositions.

In yet another embodiment of the present invention, there is provided a method of treating an individual with neurodegenerative disease involving motor neuron death in an individual in need of such treatment comprising the step of administering to the individual a pharmacologically effective dose of the instant pharmaceutical compositions or pharmacologically acceptable salts thereof.

In yet another embodiment of the present invention, there is provided a preservation solution for donor organs, the solution comprising the compounds of the present invention or a pharmacologically acceptable salt thereof.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the key to various metalloporphyrin structures. The structure of protoporphyrin IX is shown at the top left; FePPIX is equivalent to the naturally-occurring prosthetic group known as heme. The porphyrin nucleus is shown at the middle left together with R-groups. Table I lists the chemical name associated with each acronym.

FIG. 13 shows prolonged survival of ALS-SOD1 (G93A) transgenic mice treated with an iron porphyrin peroxynitrite scavenger.

DETAILED DESCRIPTION OF THE INVENTION

Figure 2:
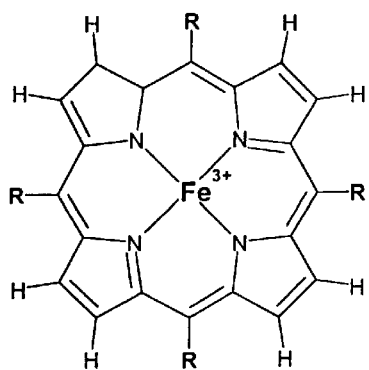
FIG. 2 shows the key to iron(III) porphyrin (Fe(III)) structures. The structure of the basic Fe(III) porphyrin nucleus with the R group substituents unidentified is shown at the top left. The substituent R groups (R1–R14) are also listed. Table II lists the chemical name associated with each R group.
Figure 2:
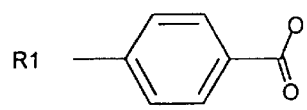
Figure 2:
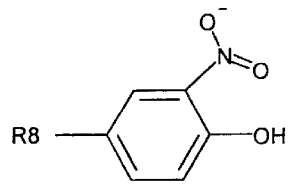
Figure 2:
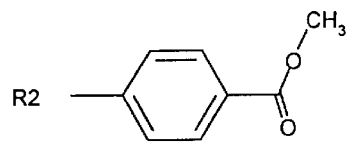
Figure 2:
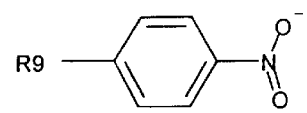
Figure 2:
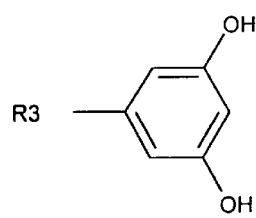
Figure 2:
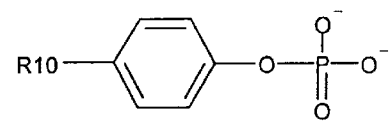
Figure 2:
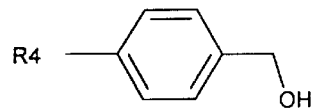
Figure 2:
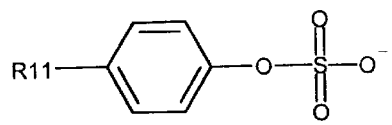
Figure 2:
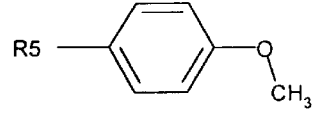
Figure 2:
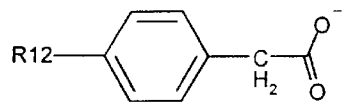
Figure 2:
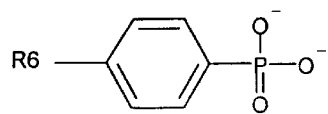
Figure 2:
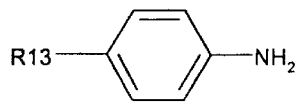
Figure 2:
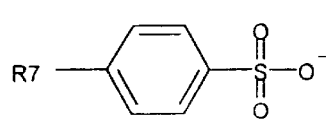
Figure 2:
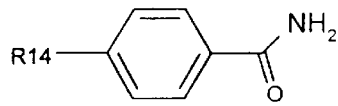

In the present invention, there is provided a compound of the formula

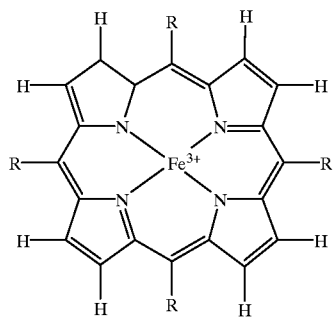

where R is selected from the group consisting of $PhCO_2CH_3$, $Ph(3,5-OH)_2$, $PhCH_2OH$, $PhOCH_3$, $PhPO_3^{-2}$, $Ph(3-NO_2-4-OH)$, $PhNO_2^-$, $PhOPO_3^{-2}$, $PhOSO_3^{-2}$, $PhCH_2CO_2^-$, $PhNH_2$, and $PhCONH_2$. Additionally, the present invention is directed to a pharmaceutical composition comprising these compounds and those additional compounds where R also may be $PhCO_2^-$ and $PhSO_3^-$ and a pharmaceutically acceptable carrier. Examples of the compounds are iron(III) meso 5,10,15,20-tetrakis-(4-carboxy)-phenyl porphyrin (FeTCPP) and iron(III) meso 5,10,15,20-tetrakis-(4-carboxymethyl)-phenyl porphyrin (FeTMeO-TCPP).

The present invention is further directed to a method of treating an individual with Amyotrophic Lateral Sclerosis in need of such treatment, comprising the step of administering to the individual a pharmacologically effective dose of the pharmaceutical compositions of the instant invention. Preferably, this composition is administered in a dose of from about 0.2 mg/kg to about 5 mg/kg of body weight. Representative examples of compounds comprising the pharmaceutical composition are iron(III) meso 5,10,15,20-tetrakis-(4-carboxy)-phenyl porphyrin (FeTCPP) and iron (III) meso 5,10,15,20-tetrakis-(4-carboxymethyl)-phenyl porphyrin (FeTMeO-TCPP) and a pharmaceutically acceptable carrier.

In yet another embodiment of the present invention, there is provided a method of treating an individual with neurodegenerative disease involving motor neuron death in an individual in need of such treatment, comprising the step of administering to the individual a pharmacologically effective dose of the instant pharmaceutical compositions or pharmacologically acceptable salts thereof. Preferably, the pharmaceutical compositions or pharmacologically acceptable salts thereof are administered in a dose of from about 0.2 mg/kg to about 5 mg/kg of body weight. Representative examples of compounds comprising the pharmaceutical composition are iron(III) meso 5,10,15,20-tetrakis-(4-carboxy-phenyl)porphyrin (FeTCPP) and iron(III) meso 5,10,15,20-tetrakis-(4-carboxymethyl-phenyl)porphyrin (FeTMeO-TCPP) and a pharmaceutically acceptable carrier. Representative neurodegenerative diseases include Amyotrophic Lateral Sclerosis (ALS), a spinal cord injury, traumatic spinal cord injury, Parkinson's Disease, and neurodegeneration due to neurotoxic agents such as 1-methyl-4-phenyl-1,2,3,6-tetrahydro pyridine (MPTP) (45). These methods of the present invention may be particularly useful in treating neurodegenerative diseases characterized by oxidative injury, especially in situation where the oxidative injury is mediated by peroxynitrite.

The present invention is also directed to a preservation solution for donor organs, said solution comprising the compounds of the present invention or a pharmacologically acceptable salt thereof. Preferably, the compounds of the present invention o r pharmacologically acceptable salts thereof are contained in the solution in a concentration of from about 0.01 $\mu$M to about 10 $\mu$M. Representative examples of the preservation solution contain iron(III) meso 5,10,15,20-tetrakis-(4-carboxy)-phenyl porphyrin (FeTCPP) and iron(III) meso 5,10,15,20-tetrakis-(4-carboxymethyl)-phenyl porphyrin (FeTMeO-TCPP).

It is specifically contemplated that pharmaceutical compositions may be prepared using the iron (III)porphyrin compounds of the present invention. In representative cases, the pharmaceutical composition comprises iron(III) meso 5,10,15,20-tetrakis-(4-carboxy)-phenyl porphyrin (FeTCPP) or iron(III) meso 5,10,15,20-tetrakis-(4-carboxymethyl)-phenyl porphyrin (FeTMeO-TCPP) and a pharmaceutically acceptable carrier. A person having ordinary skill in this art would readily be able to determine, without undue experimentation, the appropriate dosages and routes of administration of the iron (III)porphyrins of the present invention.

Administration of the compositions of the present invention may be by topical, intraocular, parenteral, oral, intranasal, intravenous, intramuscular, intrathecal, subcutaneous, or any other suitable means. The dosage administered is dependent upon the age, clinical stage and extent of the disease or genetic predisposition of the individual, location, weight, kind of concurrent treatment, if any, and nature of the pathological or malignant condition. The effective delivery system useful in the method of the present invention may be employed in such forms as capsules, tablets, liquid solutions, suspensions, or elixirs, for oral administration, or sterile liquid forms such as solutions, suspensions or emulsions. For topical use it may be employed in such forms as ointments, creams or sprays. Any inert carrier is preferably used in combination with suitable solubilizing agents, such as saline, or phosphate-buffered saline, or any such carrier in which the compounds used in the method, such as ethanol, acetone, or DMSO, of the present invention have suitable solubility properties.

Compounds of the present invention, pharmaceutically acceptable salt thereof and pharmaceutical compositions incorporating such, may be conveniently administered by any of the routes conventionally used for drug administration, e.g., orally, topically, parenterally, or by inhalation. In the case of neurodegenerative diseases such as ALS or traumatic spinal cord injury, intrathecal delivery may be the preferred route of administration. The compounds of the present invention, such as iron(III) meso 5,10,15,20-tetrakis-(4-carboxy)-phenyl porphyrin (FeTCPP) and iron(III) meso 5,10,15,20-tetrakis-(4-carboxymethyl)-phenyl porphyrin (FeTMeO-TCPP) may be administered in conventional dosage forms prepared by combining the compound with standard pharmaceutical carriers according to conventional procedures. The instant iron(III)porphyrins may also b e administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well known variable. The carrier(s) must be "acceptable" in the sense of being compatible with the other ingredients of the formulation and not deleterious to the recipient thereof.

The pharmaceutical carrier employed may be, for example, either a solid or a liquid. Representative solid carriers are lactose, terra alba, sucrose, talc, gelatin, agar, pectin, acacia, magnesium sterate, stearic acid and the like. Representative liquid carriers include syrup, peanut oil, olive oil, water and the like. Similarly, the carrier may include time delay material well known in the art such as glyceryl monosterate or glyceryl disterarate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension.

The iron(III)porphyrins of the present invention may be administered topically (non-systemically). This includes the application of 2-bromopalmitate externally to the epidermis or the buccal cavity and the instillation of such a compound into the ear, eye and nose, such that the compound does not significantly enter the bloodstream. Formulation suitable for topical administration include liquid or semi-liquid preparations suitable for penetration through the skin to the site of inflammation such as liniments, lotions, creams, ointments, pastes and drops suitable for administration to the ear, eye and nose. The active ingredient may comprise, for topical administration from 0.001% to 10% w/w, for instance from 1% to 2% by weight of the Formulation. It may however, comprise as much as 10% w/w but preferably will comprise less than 5% w/w, more preferably from 0.1% to 1% w/w of the Formulation.

Lotions according to the present invention include those suitable for application to the skin and eye. An eye lotion may comprise a sterile aqueous solution optionally containing a bactericide and may be prepared by methods similar to those for the preparation of drops. Lotions or liniments for application to the skin may include an agent to hasten drying and to cool the skin, such as an alcohol or acetone, and/or a moisterizer such as glycerol or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap, a mucilage, an oil of natural origin such as almond, corn, archis, castor, or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as siliceous silicas, and other ingredients such as lanolin may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving. Alternatively, the solution may be sterilized by filtration and transferred to the container by an aseptic technique. Examples of bactericidal and fungicidal agents suitable for inclusion in the drops are phenymercuric nitrate or acetate (~0.002%), benzalkonium chloride (~0.01%) and chlorhexidine acetate (~0.01%). Suitable solvents for the preparation of an oily solution include glycerol, diluted alcohol and propylene glycol.

The instant iron(III)porphyrins may be administered parenterally, i.e., by intravenous, intramuscular, subcutaneous, intranasal, intrathecal, intrarectal, intravaginal or intraperitoneal administration. The subcutaneous and intramuscular forms of parenteral administration are generally preferred. Appropriate dosage forms for such administration may be prepared by conventional techniques. Compounds may also be administered by inhalation, e.g., intranasal and oral inhalation administration. Appropriate dosage forms for such administration, such as aerosol formulation or a metered dose inhaler may be prepared by conventional techniques well known to those having ordinary skill in this art.

For all methods of use disclosed herein for the instant iron(III)porphyrins, particularly iron(III) meso 5,10,15,20-tetrakis-(4-carboxy)-phenyl porphyrin and iron(III) meso 5,10,15,20-tetrakis-(4-carboxymethyl)-phenyl porphyrin, the daily oral dosage regiment will preferably be from about 0.1 to about 5 mg/kg of total body weight. The daily parenteral dosage regimen will preferably be from about 0.1 to about 5 mg/kg of total body weight. The daily topical dosage regimen will preferably be from about 0.01 to about 100 g, administered one to four, preferably two to three times daily. It will also be recognized by one of skill in this art that the optimal quantity and spacing of individual dosages of the instant iron(III)porphyrins, or pharmaceutically acceptable salts thereof, will be determined by the nature and extent of the condition being treated and that such optimums can be determined by conventional techniques.

Suitable pharmaceutically acceptable salts are well known to those skilled in the art and include basic salts of inorganic and organic acids, such as hydrochloric acid, hydrobromic acid, sulphuric acid, phophoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of the iron(III) porphyrins of the present invention may also be formed with a pharmaceutically acceptable cation, for instance, if a substituent group comprises a carboxy moiety. Suitable pharmaceutically acceptable cations are well known in the art and include alkaline, alkaline earth ammonium and quaternary ammonium cations.

The following examples describe various protocols used to characterize the chemical properties of the metalloporphyrins in vitro. The following examples are given for the purpose of illustrating various embodiments of the invention and are not meant to limit the present invention in any fashion.

EXAMPLE 1

Materials

Metalloporphyrin compounds were purchased from Porphyrin Products, Inc., Logan, Utah. Metalloporphyrin solutions were standardized by weight and dissolved in distilled, filtered (Millipore) water. UV-visible spectra were determined for all MPs. Highly resolving HPCL-UV analysis of FeTCPP used for cell and animal experiments indicated that the preparation was >97.5% pure. In addition, MnTMPyP and MnTBAP were analyzed by HPLC-UV and found to be chromatographically identical to the respective preparations obtained from Alexis Biochemicals. MPs from Porphyrin Products, Inc. were used for all studies. Phosphate and borate buffers were treated with Chelex 100 resin to remove trace metals prior to use. Glycine-tyrosine-alanine tripeptide (GYA), 3-hydroxyphenlacetic acid (HPA), ascorbic acid, and glutathione (GSH) were obtained from Sigma Chemical Co. Dichlorodihydrofluorescein diacetate (DCDHF-DA) was obtained from Molecular Probes, Inc., Eugene, Oreg. The diacetate groups of DCDHF-DA were cleaved immediately prior to use by dissolving DCDHF-DA in 20 mM NaOH followed by neutralization with 0.1 M potassium phosphate, pH 7.4. The resulting DCDHF solution was wrapped in foil and kept at 4° C.

EXAMPLE 2

Metalloporphyrin Nomenclature and Structures

Most metalloporphyrins are symmetrical, with four identical functional groups extending out from the cyclic tetrapyrrole which binds the metal atom. The nature of these functional groups dramatically affects both the redox properties of the metal and the ability to bind other macromolecules within the cell. For example, the tetra-4-methylpyridyl porphyrins (TMPyP) possess four permanent positive charges and readily intercalate into DNA whereas the negatively charged tetra-4-carboxyphenyl porphyrins (e.g., FeTCPP) do not appear to bind cellular components and, therefore, are free to scavenge peroxynitrite in any cellular compartment. Side chain-mediated effects on redox properties are evidenced by the different reactivities with peroxynitrite and the differential catalysis of nitrative and oxidative reactions.

The names and acronyms of general metalloporphyrin compounds are listed in Table I and the structures in FIG. 1. Table II names novel Fe(III)porphyrins and further identifies the substituent R groups containing cationic, anionic or uncharged functional groups on these compounds. The structures of the compounds identified in Table II are found in FIG. 2.

TABLE I

| Key to Metalloporphyrin Acronyms | |
|---|---|
| MnTMPyP | Manganese (III) meso-tetra-(N-methyl-4-pyridyl)-porphine chloride |
| MnPPIX | Manganese (III) protoporphyrin IX dichloride |
| MnTBAP | Manganese (III) tetra-(4-benzoic acid)-porphyrin |
| FeTMPyP | Iron (III) meso-tetra-(N-methyl-4-pyridyl)-porphine chloride |
| FePPIX | Iron (III) protoporphyrin IX dichloride |
| FeTSPP | Iron (III) meso-tetra-(4-sulfonatophenyl)-porphyrin |
| CuTMPyP | Copper (II) meso-tetra-(N-methyl-4-pyridyl)-porphine tetra tosylate |
| CuTSPP | Copper (II) meso-tetra-(4-sulfonatophenyl)-porphyrin |
| PtTMPyP | Platinum (II) meso-tetra-(N-methyl-4-pyridyl)-porphine chloride |
| PdTBAP | Paladium (II) tetra-(4-benzoic acid)-porphyrin |
| AlPCTP | Aluminum (III) phthalocyanine tetrasulfonate porphine chloride |
| ZnTBAP | Zinc (II) tetra-(4-benzoic acid)-porphyrin |

TABLE II

| R Group | Substituent Group & Compound Name |
|---|---|
| R1 | (4-carboxy-phenyl): Iron (III) meso 5,10,15,20-tetrakis-(4-carboxy-phenyl) porphyrin (FeTCPP) |
| R2 | (4-carboxymethyl-phenyl): Iron (III) meso 5,10,15,20-tetrakis-(4-carboxymethyl-phenyl) porphyrin |
| R3 | 4-(3,5-dihydroxy-phenyl): Iron (III) meso 5,10,15,20-tetrakis-4-(3,5-dihydroxy-phenyl) porphyrin |
| R4 | (4-hydroxymethyl-phenyl): Iron (III) meso 5,10,15,20-tetrakis-(4-hydroxymethyl-phenyl) porphyrin |
| R5 | (4-O-methyl-phenyl): Iron (III) meso 5,10,15,20-tetrakis-(4-O-methyl-phenyl) porphyrin |
| R6 | (4-phospho-phenyl) Iron (III) meso 5,10,15,20-tetrakis-(4-phospho-phenyl) porphyrin |
| R7 | (4-sulfo-phenyl): Iron (III) meso 5,10,15,20-tetra-(4-sulfo-phenyl)-porphyrin |
| R8 | (3-nitro-4-hydroxy-phenyl): Iron (III) meso 5,10,15,20-tetrakis-(3-nitro-4-hydroxy-phenyl) porphyrin |
| R9 | (4-nitro-phenyl): Iron (III) meso 5,10,15,20-tetrakis-(4-nitro-phenyl) porphyrin |
| R10 | (4-O-phosphophenyl): Iron (III) meso 5,10,15,20-tetra-(4-O-phosphophenyl) porphyrin |
| R11 | (4-O-sulfophenyl): Iron (III) meso 5,10,15,20-tetra-(4-O-sulfophenyl) porphyrin |
| R12 | (4-phenylacetic acid): Iron (III) meso 5,10,15,20-tetrakis-(4-phenylacetic acid) porphyrin |
| R13 | (4-amino-phenyl): Iron (III) meso 5,10,15,20-tetrakis-(4-amino-phenyl) porphyrin |
| R14 | (4-amidophenyl): Iron (III) meso 5,10,15,20-tetrakis-(4-amido-phenyl) porphyrin |

EXAMPLE 3
GSH Oxidation

Glutathione (GSH) oxidation in the absence and presence of MPs was measured by incubating either FeTMPyP, MnTMPyP, and CuTMPyP (at 5 $\mu$M final concentration) with 2 mM GSH in 2 ml of 0.1 M potassium phosphate buffer, pH 7.4 in a stirred cuvette at 37° C. Aliquots (14 $\mu$l) were removed at 10 min intervals and added to 1.4 of 0.1 M potassium phosphate, pH 7.4 containing 0.2 mM dithionitrobenzoic acid (Ellman's Reagent) and 50 $\mu$M EDTA. GSH concentration was determined by the change in 430 nm absorbance. The extinction coefficient at 430 nm was determined to be 13,900 $M^{-1}cm^{-1}$ using a fresh GSH solution standardized by weight.

EXAMPLE 4
Peroxynitrite Synthesis and Standardization

Peroxynitrite was prepared as described previously (17). Briefly, an aqueous solution of 0.6 M sodium nitrite was rapidly mixed with an equal volume of 0.7 M hydrogen peroxide containing 0.6 M HCl and immediately quenched with the same volume of 1.5 M NaOH. All reaction solutions were kept on ice. The concentration of peroxynitrite was determined spectrally in 0.1 M NaOH ($\epsilon$302 nm=1,670 M-1cm-1) (18). The concentration of freshly synthesized peroxynitrite solutions was typically 150 mM 180 mM (75% of theoretical yield) leaving a 25% contamination (50 mM) by of $H_2O_2$ and nitrite. Thus, when 20 $\mu$M peroxynitrite was used to oxidize Mn porphyrins, 5 $\mu$M each of $H_2O_2$ and nitrite were present. Tetramethylammonium peroxynitrite (purchased from Alexis), which has no $H_2O_2$ contamination, was used to assess any interference due to $H_2O_2$. $H_2O_2$ increased the rate of re-reduction of Mn(IV)porphyrins back to their respective Mn(III) forms, apparently via direct reduction of the Mn(IV)=O intermediate. However, the rate of $H_2O_2$-mediated re-reduction was roughly 1500-fold slower than oxidation of Mn(III)porphyrins by peroxynitrite. Thus, interference with peroxynitrite-mediated metalloporphyrin oxidation by the low micromolar amounts of $H_2O_2$ present was negligible.

EXAMPLE 5
Rate Constants for Metalloporphyrin Oxidation by Stopped-flow Spectroscopy Rates of metal loporphyrin oxidation by peroxynitrite were determined using a Bio Sequential SX-18MV Applied Photophysics stopped-flow spectrofluorometer. Metalloporphyrins and peroxynitrite were loaded into separate syringes at 2-fold higher concentrations than indicated in Table III. Solutions of metalloporphyrins in 0.1 M potassium phosphate buffer, pH 7.4 were placed in one syringe and solutions of peroxynitrite in 10 mM NaOH were placed in a second syringe, both of which were submerged in a water bath at 37° C. Changes in metalloporphyrin absorbance as a function of time were recorded following triggering of syringe firing and solution mixing (instrument dead time=2 msec); a total of 1000 data points were collected over intervals ranging from 50 msec to 3 sec. The appearance of Mn(IV) and Fe(IV) forms and the disappearance of Mn(III) and Fe(III) forms were monitored at their corresponding wavelengths and found to agree temporally. Because the absorbance changes associated with loss of +3 forms were greater, rates of metalloporphyrin oxidation were determined by monitoring the disappearance of Mn(III)TMPyP at 462 nm, Mn(III)TBAP at 468 nm, Mn(III)PPIX at 466 nm, and Fe(III)PPIX at 464 nm. Absorbance changes as a function of time were fitted to the equation describing a first order process. The concentration of peroxynitrite was varied from five-fold to forty-fold greater than the fixed metalloporphyrin concentration in order to obtained pseudo first-order conditions (see Table III). Each concentration was injected 10 times and data were averaged automatically prior to fitting.

EXAMPLE 6
Rate Constants for Metalloporphyrin-catalyzed Peroxynitrite Decomposition.

Figure 5A:
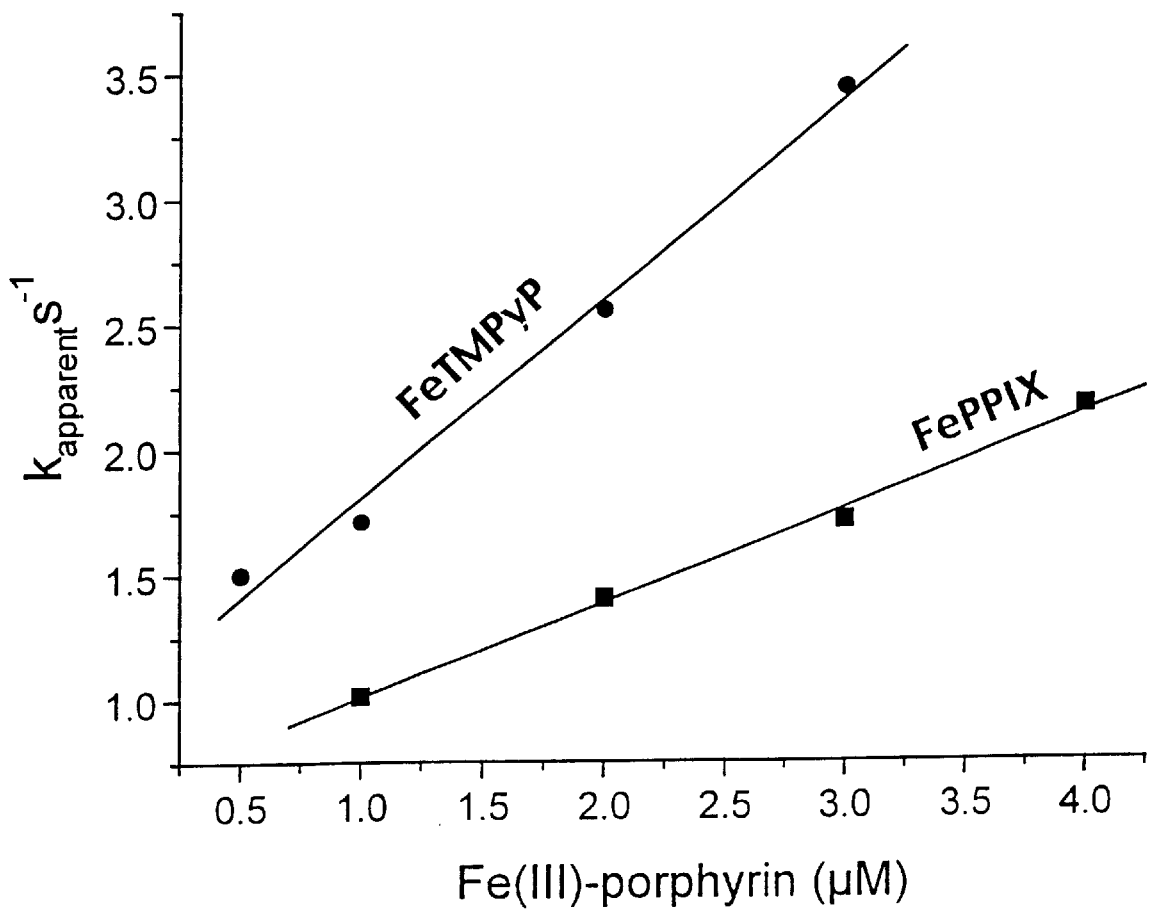
FIG. 5 shows the rates of peroxynitrite decomposition as a function of Fe(III)-porphyrins (FIG. 5A) and MnTMPYP (FIG. 5B) concentrations. Peroxynitrite (100 $\mu$M) was added to rapidly stirred cuvettes at 37° C. containing the indicated concentrations of MPs in 0.1 M potassium phosphate, pH 7.4. Ascorbate was added to 150 $\mu$M where indicated. Peroxynitrite decomposition was monitored at 302 nm using a Hewlett-Packard diode-array spectrophotometer. Apparent rates ($k_{apparent}s^{-1}$, average of n=3) were plotted versus MP concentration to determine rate constants in $M^{-1}s^{-1}$.
Figure 5B:
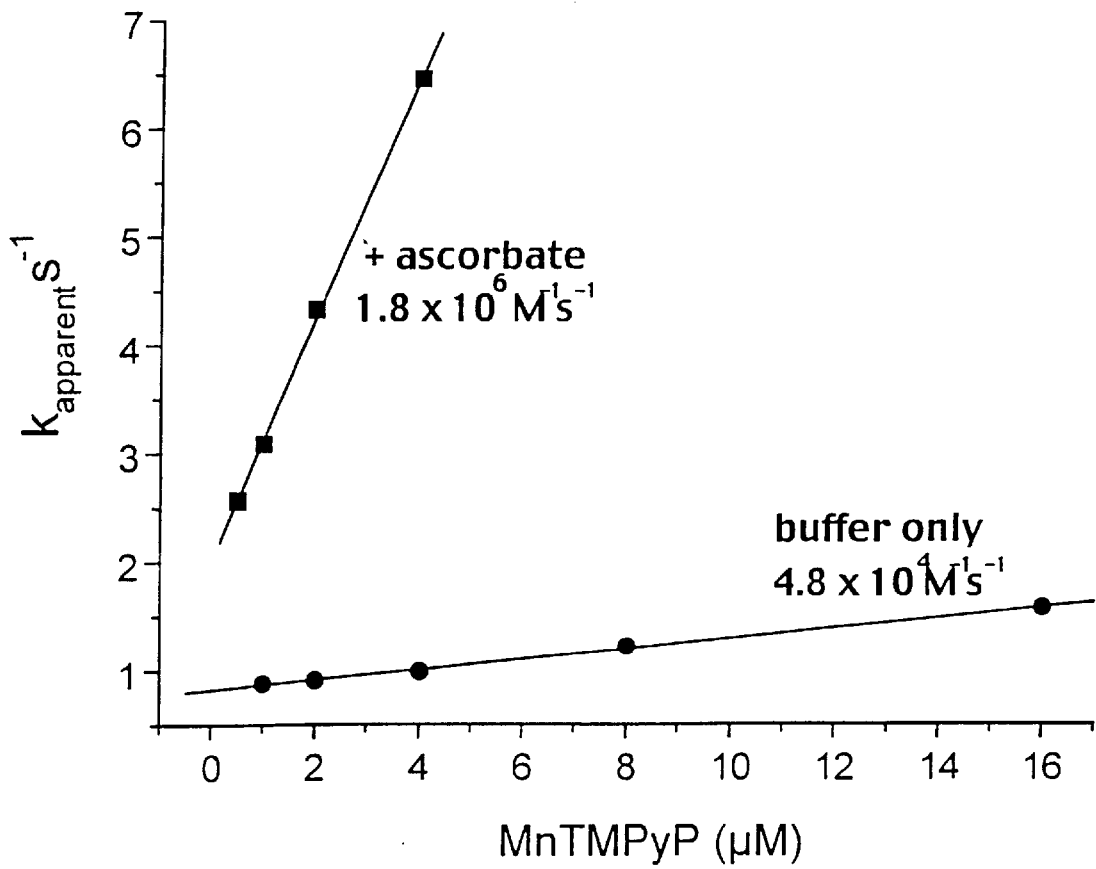

Peroxynitrite (100 $\mu$M) decomposition was determined at 302 nm using a Hewlett-Packard diode-array spectrophotometer fitted with a temperature-controlled cuvette chamber and a water-driven cuvette stirrer. Bolus additions of peroxynitrite were made to vigorously stirred cuvettes containing varying concentrations of MPs (see Table III) while data were collected at a rate of ten points/sec. Three separate additions of peroxynitrite were made sequentially to each reaction solution to assess the extent of peroxynitrite-mediated inactivation of metalloporphyrin, i.e., a progressive slowing of the rate of peroxynitrite decomposition was suggestive of metalloporphyrin inactivation. Each reaction was repeated three times and only the first additions of peroxynitrite were averaged. Data were exported for fitting and plotting. Apparent rates of peroxynitrite decomposition were plotted as a function of metalloporphyrin concentration (as shown in FIG. 5) to determine concentration-independent rate constants at 37° C. Ascorbate (150 $\mu$M) was added to the two manganese porphyrins which displayed slow re-reduction of the Mn(IV) intermediate (MnTMPyP and MnTBAP) immediately prior to adding peroxynitrite. The slight increase in the rate of peroxynitrite decomposition due to ascorbate alone was determined and subtracted from the rates seen with manganese porphyrin plus ascorbate.

EXAMPLE 7
Nitration Efficiency using GYA Peptide or HPA

For nitration of GYA peptide (see FIG. 6), reaction solutions contained 2 mM GYA and 10 $\mu$M of the indicated MP in 1.4 ml of 0.1 M potassium phosphate, pH 7.4 at 37° C. Comparisons with two previously characterized nitration catalysts, human Cu,Zn superoxide dismutase (hCu,Zn SOD) and carbon dioxide, were made using 10 $\mu$M of SOD subunit and 25 mM potassium bicarbonate, respectively, which was pH-adjusted to 7.4. This level of bicarbonate results in rapid saturation of the solution with carbon dioxide (~1 mM). Solutions were placed into a rapidly stirred cuvette and nine bolus additions (50 $\mu$M×3, 100 $\mu$M×3, and 200 $\mu$M×3) of peroxynitrite were made sequentially while the absorbance was monitored. Increasing amounts of peroxynitrite were added in a sequential manner in order to determine whether nitration efficiency varied with concentration and to determine whether nitration catalysis was maintained with multiple additions (see FIG. 6 inset). Nitration efficiency was defined as the amount of nitropeptide formed per amount of peroxynitrite added and was calculated for each peroxynitrite addition; the values shown are the average of all nine peroxynitrite additions. The absorbance changes associated with nitrotyrosine peptide production were monitored simultaneously at 380, 430, and 460 nm. The extinction coefficients for nitrated GYA at pH 7.4 are 4,400 $M^{-1}cm^{-1}$ at 430 nm and 2,200 $M^{-1}cm^{-1}$ at both 380 and 460 nm. Previous studies have revealed that nitrotyrosine has the same extinction coefficient at these wavelengths regardless of whether it is present in a peptide or present as the free amino acid (19). Wavelengths used to quantify nitrotyrosine production were chosen to minimize interference by the particular metalloporphyrin used.

Experiments using HPA as a nitration target (FIG. 7) contained 8 mM HPA in either 0.1 M potassium phosphate, pH 7.4 or 0.1 M sodium borate, pH 9.1.

EXAMPLE 8

Oxidation by Peroxynitrite

Figure 3A:
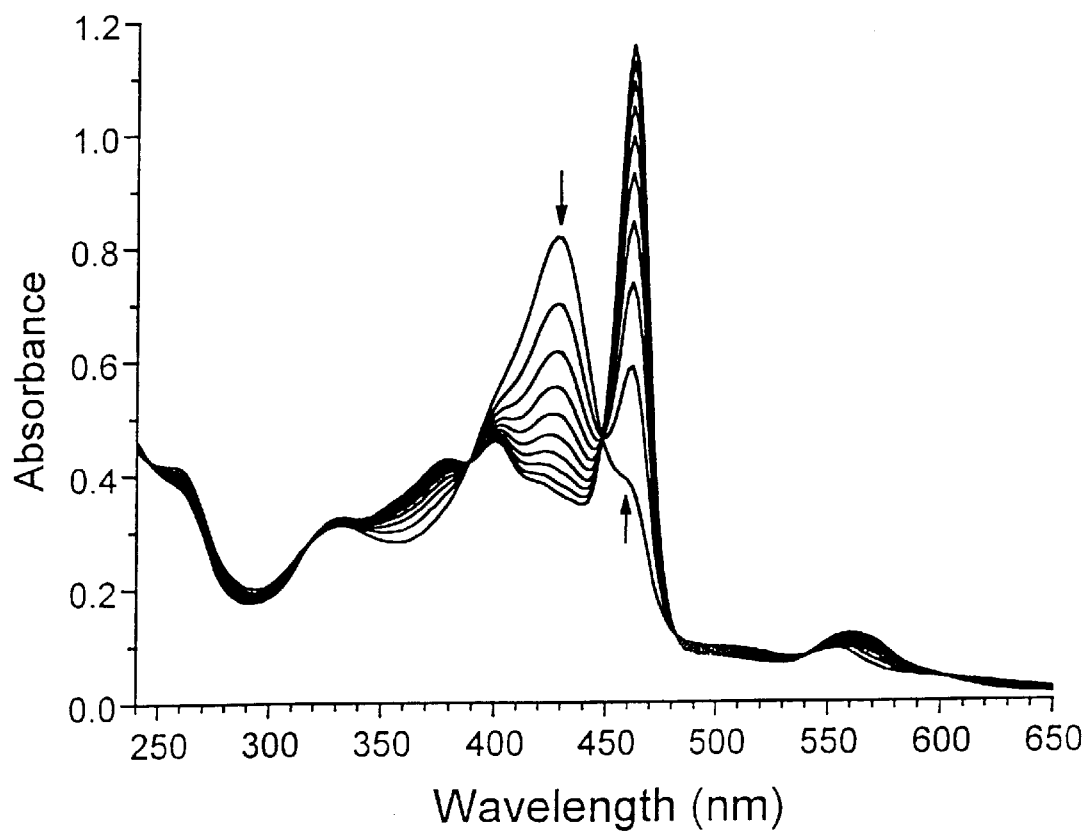
FIGS. 3A and 3B show the re-reduction of peroxynitrite-oxidized MnTMPyP and MnTBAP. Bolus additions of peroxynitrite (20 $\mu$M) were added to rapidly stirred cuvettes at 37° C. containing the indicated either (FIG. 3A) MnTMPyP (10 $\mu$M) or (FIG. 3B) MnTBAP (10 $\mu$M) in 0.1 M potassium phosphate buffer, pH 7.4. Wavelength scans were initiated 1 s after peroxynitrite addition and repeated at 3 s intervals; the spectral changes seen are associated with the re-reduction of the +4 forms to +3. The peaks at 428 nm (left arrows) are due to Mn(IV)=O (15) whereas the 464 nm peaks (right arrows) are due to Mn(III). Because the reappearance of the Mn(III) peaks at 464 nm corresponds temporally to the loss of the Mn(IV)=O peaks, either absorbance change could be used for monitoring oxidation and subsequent re-reduction. INSET: The indicated amounts of peroxynitrite were added to solutions of MnTBAP (10 $\mu$M) in phosphate buffer and the decrease in 464 nm absorbance was monitored at a data collection rate of 10 points/s. The maximal change in 464 nm absorbance associated with oxidation of Mn(III) to Mn(IV), which occurred in >1 s, was plotted versus peroxynitrite; the concentration at which no further absorbance change occurred was used to establish the reaction stoichiometry.
Figure 3B:
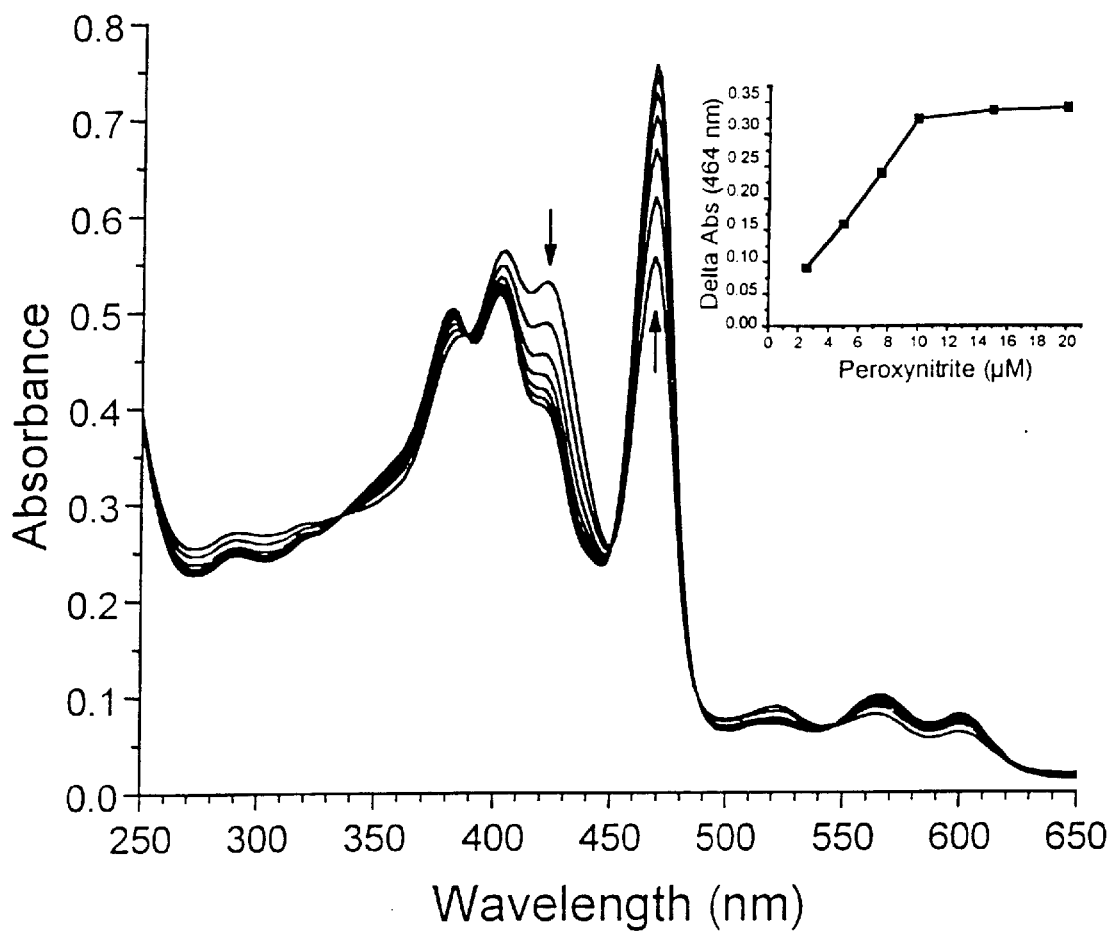

The metalloporphyrins Mn(III)TMPyP and Mn(III)TBAP (see Table I for key to acronyms and FIG. 1 for structures) were rapidly and completely oxidized by a 2-fold molar excess of peroxynitrite. Spectral scans initiated immediately after oxidation by peroxynitrite reveal that re-reduction to the Mn(III) forms is relatively slow (FIGS. 3A and 3B). Spectral changes seen in these figures are consistent with formation of Mn(IV)=O intermediates (420–430 nm) followed by re-reduction to the parent Mn(III)-porphyrins (460–470 nm) as has been reported previously for MnTMPyP (8,12,13,15). Based on the maximal absorbance change immediately following peroxynitrite addition (equivalent to the first scan shown in FIG. 3B), the dose-response for peroxynitrite-mediated oxidation of MnTBAP revealed a stoichiometry of 1:1 (FIG. 3B, inset).

In order to assess whether other biologically relevant oxidants were capable of oxidizing metalloporphyrins, MnTMPyP and FeTMPyP were treated with hydrogen peroxide ($H_2O_2$) and hypochlorous acid (HOCl). Incubation with $H_2O_2$ (0.5 mM) resulted in slow decreases in the primary absorbance peaks of MnTMPyP and FeTMPyP (464 and 424 nm, respectively), but the changes were quite small even after 20 min (not shown). Treatment of these two metalloporphyrins with 50 µM HOCl resulted in immediate and irreversible loss of soret bands consistent with metalloporphyrin decomposition. Thus, $H_2O_2$ did not appear to oxidize MnTMPyP or FeTMPyP and HOCl appeared to destroy the metal-pyrrole center.

EXAMPLE 9

Rate Constants for Reaction of Peroxynitrite with Metalloporphyrins

Figure 4:
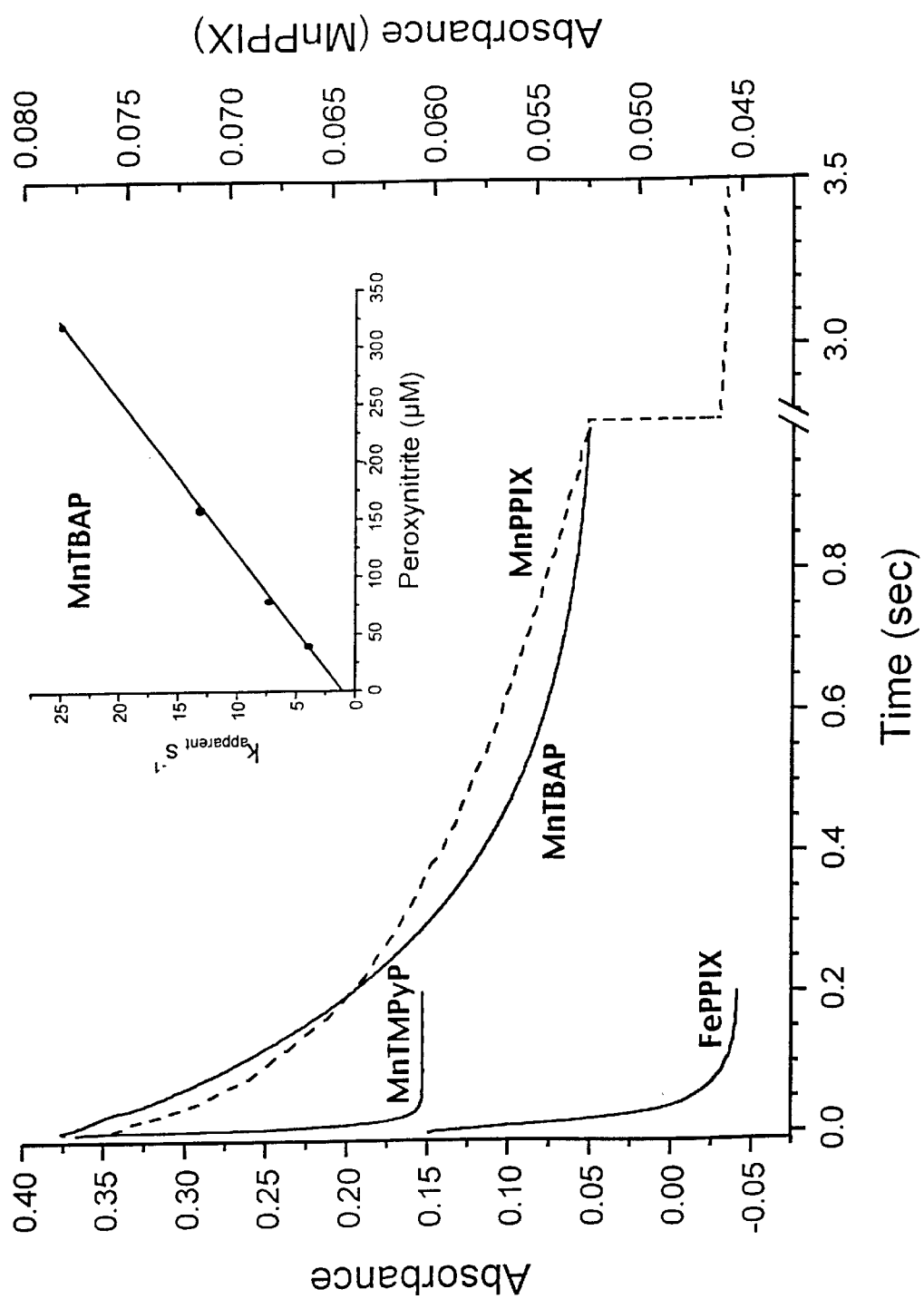
FIG. 4 shows the oxidation of MPs by peroxynitrite. Peroxynitrite (in 10 mM NaOH) was rapidly mixed with the indicated MPs in 0.1 M potassium phosphate, pH 7.4 at 37° C. using a stopped-flow apparatus as described in Methods. For the stopped-flow traces shown, a solution of 40 $\mu$M peroxynitrite was added to an equal volume of an 8 $\mu$M MnTMPyP solution to give final concentrations of 20 $\mu$M and 4 $\mu$M, respectively. A final concentration of 40 $\mu$M peroxynitrite was added to 8 $\mu$M of each of the MPs MnTBAP, MnPPIX, and FePPIX. Oxidation of MnTMPyP was monitored at 464 nm, MnTBAP at 470 nm, MnPPIX at 464 nm, and FePPIX at 387 nm. INSET: Apparent rate constants for oxidation of 8 $\mu$M MnTBAP are plotted as a function of peroxynitrite concentration to illustrate how the rate constants listed in Table III were determined.

Rate constants for stoichiometric metalloporphyrin oxidation by peroxynitrite at 37° C. were determined under pseudo-first order reaction conditions by varying the amount of peroxynitrite added to a fixed concentration of metalloporphyrin (Table III). These rate constants indicate how rapidly peroxynitrite reacts with each metalloporphyrin and thus, provide a predictive index of how well each metalloporphyrin could compete with biomolecules for the available peroxynitrite. The metalloporphyrins listed in Table III were the only ones where spectral changes associated with peroxynitrite-mediated oxidation were of sufficient magnitude and duration to permit accurate rate determinations at 37° C. Stopped-flow traces for oxidation of MnTMPyP (4 µM), MnTBAP (8 µM), MnPPIX (8 µM), and FePPIX (8 µM) by a five-fold molar excess of peroxynitrite in each case are shown in FIG. 4. The inset of FIG. 4 shows the apparent rate constants for stoichiometric oxidation of MnTBAP (8 µM) at different peroxynitrite concentrations and illustrates how the rate constants listed in Table III were determined. MnTMPyP and FePPIX were oxidized at rates of $3.6 \times 10^6$ $M^{-1}s^{-1}$ and $1.0 \times 10^6$ $M^{-1}s^{-1}$, respectively whereas two other Mn(III)-porphyrins, MnPPIX and MnTBAP, were oxidized at considerably slower rates ($9.9 \times 10^4$ $M^{-1}s^{-1}$ and $2.5 \times 10^4$ $M^{-1}s^{-1}$, respectively). A rate constant of $1.8 \times 10^6$ $M^{-1}s^{-1}$ has been reported previously for MnTMPyP (8) and was repeated here to validate provide a direct comparison with other metalloporphyrins under the same experimental conditions.

TABLE III

| Metalloporphyrin | Rate Constants for Oxidation of MPs by Peroxynitrite |
|---|---|
| MnTMPyP | $3.6 \times 10^6 \pm 0.4$ $M^{-1}s^{-1}$ |
| FePPIX | $1.0 \times 10^6 \pm 0.3$ $M^{-1}s^{-1}$ |
| MnPPIX | $9.9 \times 10^4 \pm 0.7$ $M^{-1}s^{-1}$ |
| MnTBAP | $2.5 \times 10^4 \pm 0.4$ $M^{-1}s^{-1}$ |

In Table III, the rate of peroxynitrite-mediated oxidation of metalloporphyrins at 37° C. was determined. Apparent rate constants were determined by stopped-flow spectroscopy and plotted versus the peroxynitrite concentration (as shown for MnTBAP in FIG. 4 inset) to determine the bimolecular rate constant in $M^{-1}s^{-1}$±standard error. FePPIX was monitored at 387 nm, MnPPIX at 464 nm, and MnTBAP at 470 nm.

EXAMPLE 10

Decomposition of Peroxynitrite by Metalloporphyrins

FeTMPyP has been reported to decompose peroxynitrite in a catalytic fashion to yield almost exclusively nitrate (7) whereas catalytic decomposition by MnTMPyP has been shown to be limited by the slow rate of re-reduction of its Mn(IV) form (8,12,13). Rates of peroxynitrite decomposition by these two metalloporphyrins were compared to three others in the absence of added reductants. The resulting rates are listed in Table IV and are graphically illustrated for FeTMPyP and FePPIX in FIG. 5A.

The rate constant for peroxynitrite decomposition by FePPIX ($3.7 \times 10^5$ $M^{-1}s^{-1}$) was only 2.8-fold slower than FePPIX oxidation by peroxynitrite (Tables III and IV), suggesting that the Fe(IV) intermediate forms also reacts quite fast with peroxynitrite as has been shown for Fe(IV) TMPyP (14). The rate constant for peroxynitrite decomposition by MnTMPyP ($4.8 \times 10^4$ $M^{-1}s^{-1}$) was 76-fold slower than its corresponding oxidation rate which agrees with previous reports indicating that regeneration of the Mn(III) form is rate-limiting to catalytic decomposition of peroxynitrite (12,13). Lee et al. (12) recently showed that peroxynitrite is decomposed much faster by MnTMPyP when coupled to ascorbate or the tocopherol analog Trolox. These one-electron reductants rapidly reduce Mn(IV)TMPyP back to Mn(III)TMPyP thereby completing the catalytic cycle and accelerating the decomposition of peroxynitrite. Rates of MP-catalyzed peroxynitrite (100 µM) decomposition were measured at various concentrations of MnTMPyP and MnTBAP in the presence of 150 µM ascorbate (Table IV). Under the conditions used, ascorbate alone (150 µM) accelerated peroxynitrite decomposition by only 16%. However, in the presence of ascorbate, the rate constant for peroxynitrite decomposition by MnTMPyP was 1.8 $10^6$ $M^{-1}s^{-1}$—38-fold faster than in the absence of ascorbate and only 2-fold slower than the stoichiometric oxidation of MnTMPyP by peroxynitrite (Table III). In the presence, but not the absence of ascorbate, MnTBAP was capable of catalyzing peroxynitrite decomposition albeit at a considerably slower rate than decomposition catalyzed by MnTMPyP (Table IV).

TABLE IV

Rates of MP-mediated peroxynitrite decomposition.

| Metalloporphyrin | Rate Constants for MP-Catalyzed Decomposition of Peroxynitrite (pH 7.4, 37° C.) |
|---|---|
| FeTCPP | $2.9 \times 10^6$ $M^{-1}s^{-1}$ ± 0.4 $M^{-1}s^{-1}$ |
| (plus ascorbate) | $6.0 \times 10^6$ $M^{-1}s^{-1}$ ± 0.5 $M^{-1}s^{-1}$ |
| FeTMPyP | $7.9 \times 10^5$ ± 0.9 $M^{-1}s^{-1}$ |
| FePPIX | $3.7 \times 10^5$ ± 0.2 $M^{-1}s^{-1}$ |
| FeTSPP | $3.3 \times 10^5$ ± 0.4 $M^{-1}s^{-1}$ |
| MnTMPyP | no acceleration |
| (plus ascorbate) | $1.8 \times 10^6$ ± 0.3 $M^{-1}s^{-1}$ |
| MnTBAP | no acceleration |
| (plus ascorbate) | $3.3 \times 10^4$ ± 0.4 $M^{-1}s^{-1}$ |
| ZnTBAP | $5.3 \times 10^3$ ± 0.3 $M^{-1}s^{-1}$ |

Rates of peroxynitrite (100 $\mu$M) decomposition were determined at different MP concentrations. Ascorbate was added to 150 $\mu$M where indicated. FeTMPyP was varied from 0.5 to 3 $\mu$M, FePPIX from 1 to 4 $\mu$M, FeTSPP from 0.5 to 8 $\mu$M, MnTMPyP from 1 to 8 $\mu$M, and MnTBAP and ZnTBAP were varied from 2 to 16 $\mu$M. Apparent rate constants were plotted versus MP concentration (as in FIG. 5A,B) to determine true rate constants in $M^{-1}s^{-1}$±standard error.

EXAMPLE 11
Re-reduction of Mn(IV)TMPyP by $H_2O_2$

Sequential additions of peroxynitrite to MnTMPyP in phosphate buffer resulted in progressively faster rates of peroxynitrite decomposition, suggesting that a buildup of end-products was contributing to catalytic decomposition. Because peroxynitrite decomposes principally to nitrate, and because nitrite and $H_2O_2$ are significant (~25%) contaminants of peroxynitrite stock solutions, these three components were tested separately for their ability to affect the rate of Mn(IV)TMPyP re-reduction following peroxynitrite addition.

Using the same concentrations of MnTMPyP (10 $\mu$M) and peroxynitrite (20 $\mu$M, containing 5 $\mu$M each of $H_2O_2$ and nitrite) as used in FIGS. 3A and 3B, the rate of re-reduction of Mn(IV)TMPyP was determined in the presence of $H_2O_2$, nitrite, or nitrate added to the reaction solution immediately before peroxynitrite. Complete re-reduction to Mn(III) TMPyP occurred in 30 s following oxidation by peroxynitrite (20 $\mu$M) alone. When 50 $\mu$M $H_2O_2$ was added immediately before peroxynitrite, complete re-reduction occurred in 17 s suggesting that $H_2O_2$ was capable of reducing the Mn(IV) intermediate. Addition of 50 $\mu$M nitrate before peroxynitrite slowed re-reduction to 74 s whereas complete re-reduction was unchanged (30 s) by pre-addition of 50 $\mu$M nitrite. When $H_2O_2$ and nitrate or $H_2O_2$ and nitrite were added together, the rate of re-reduction was the same as with $H_2O_2$ alone (17 s) indicating that re-reduction by $H_2O_2$ predominated.

Thus, a buildup of $H_2O_2$ could account for the progressive increase in the rate of peroxynitrite decomposition with MnTMPyP. Because the rate of Mn(IV) re-reduction by $H_2O_2$ was at least 1500-fold slower than Mn(III) oxidation by similar concentrations of peroxynitrite, interference by $H_2O_2$ in peroxynitrite-mediated oxidation rate constant determinations was not significant. By comparison, sequential additions of peroxynitrite to all Fe(III)-porphyrins resulted in progressively slower rates of peroxynitrite decomposition which were unaffected by prior additions of $H_2O_2$ (50 $\mu$M), nitrite (50 $\mu$M), or nitrate (50 $\mu$M) (not shown). Thus, in the case of the Fe(III)-porphyrins, progressive slowing of peroxynitrite decomposition would appear to reflect loss of catalytic activity.

Figure 6:
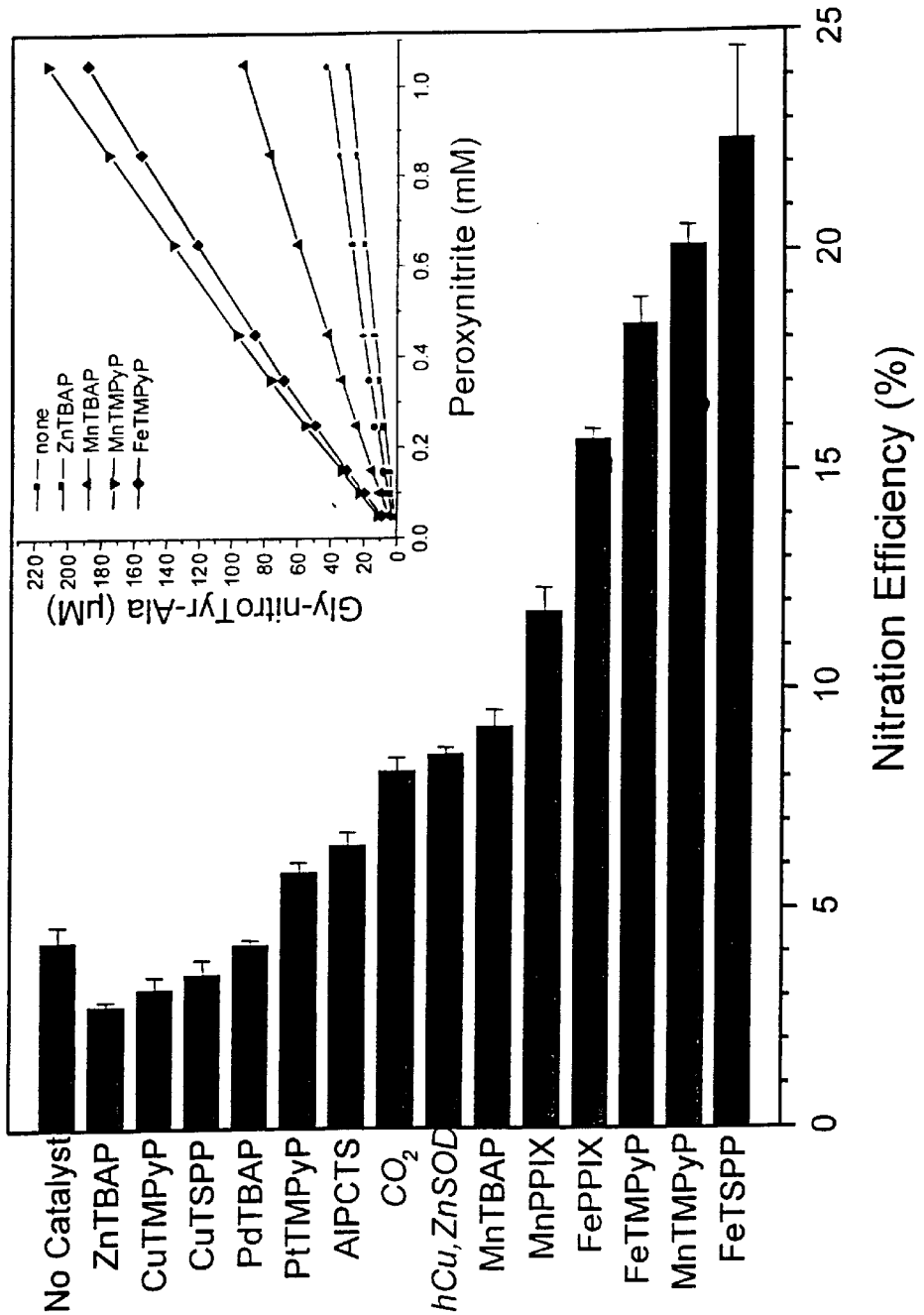
FIG. 6 shows the effects of catalysts on peroxynitrite-mediated peptide nitration. Nitration efficiency, defined as the moles of nitrated GYA peptide formed per mole of peroxynitrite added, was determined at a fixed concentration of 10 $\mu$M MP or Cu,Zn SOD subunit, or 1 mM $CO_2$ as described below. Increasing amounts of peroxynitrite were added in a sequential manner in order to determine whether nitration efficiency varied with concentration and to determine whether nitration catalysis was maintained with multiple additions (see INSET). Nitration efficiency was calculated for each peroxynitrite addition; the values shown are the average of all nine peroxynitrite additions. Absorbance changes were monitored simultaneously at 380, 430, and 460 nm.

EXAMPLE 12
Enhancement of Peroxynitrite-mediated Nitration Yields by Metalloporphyrins Peroxynitrite is a potent oxidant and nitrating agent and both MnTMPyP and MnTBAP have been reported to increase the yield of nitrated phenolics from peroxynitrite (15,9,16), however no systematic comparison of nitration catalysis by Mn- or Fe-porphyrins has been conducted. The relative abilities of several MPs to enhance nitration of the tripeptide GYA was compared using 10 $\mu$M MP and sequential bolus additions of 50 $\mu$M (×3), 100 $\mu$M (×3), and 200 $\mu$M (×3)peroxynitrite (FIG. 6, inset). The linear increase in nitro-GYA (FIG. 6, inset) as a function of repeated peroxynitrite addition indicates that nitration enhancement is a catalytic property of metalloporphyrins which is not lost upon repeated peroxynitrite exposure. The fact that MP-catalyzed nitration of GYA remained constant with repeated peroxynitrite strongly suggests that the tyrosine-containing substrate is acting as the reductant for the Mn(IV) and Fe(IV) intermediate forms—a reaction mechanism which would yield tyrosyl radical as a secondary intermediate.

A proposed mechanism for production of the nitrating species from Mn-porphyrins and inhibition by reductants is that Mn-porphyrins are oxidized to their respective +4 forms by peroxynitrite. Results of this and other studies strongly indicate that tyrosine (or other phenolic compounds) are directly oxidized by the Mn(IV)=O to yield tyrosyl radical. Nitrogen dioxide (—$NO_2$) will add to tyrosyl radical at a rate of $3 \times 10^9$ $M^{-1}s^{-1}$ (44) to give 3-nitrotyrosine. Ascorbate will rapidly reduce the Mn(IV)=O intermediate back to the stable +3 state (12,13). In addition, ascorbate will rapidly reduce nitrogen dioxide to nitrite ($NO_2^-$) and tyrosyl radical back to parent tyrosine. Thus, ascorbate can potentially inhibit formation of nitrotyrosine in three ways a s indicated by the open arrows.

FIG. 6 illustrates the average nitration efficiency, expressed as a percent of added peroxynitrite, for the nine peroxynitrite additions. Under these conditions, FeTSPP enhanced the nitration yield 5.3-fold, followed closely by MnTMPyP and FeTMPyP. By comparison, the endogenous nitration catalysts Cu,Zn superoxide dismutase (10 $\mu$M) (20) and carbon dioxide (1 mM) (21) enhanced nitration yields by 2-fold and 1.7-fold, respectively. The only other transition metal-containing porphyrins, CuTMPyP and CuTSPP, had a small but reproducible inhibitory effect on nitration as did ZnTBAP (FIG. 6).

EXAMPLE 13
Interaction of Metalloporphyrins with Ascorbate and GSH

MnTMPyP has been reported to exist in the reduced form (Mn[II]) in *E. coli* based on a change in color from reddish-brown to green over time (22). Ultrafiltration experiments suggested that the Mn(II) form was bound to macromolecules within the cells which may have served to stabilize the Mn(II) form (22). During the course of the present study, it was reported that both MnTMPyP and MnTBAP turned green over time after being taken up by primary cultures of motor neurons (23).

In order to test the hypothesis that Mn(II)- or Fe(II)-porphyrins would be capable of carrying out two-electron reductions of peroxynitrite and thereby decreasing rather than increasing its reactivity, attempts were made to pre-reduce these transition metal-containing MPs prior to addition of peroxynitrite. MPs were treated with large molar excesses of reductants like ascorbate, trolox, cysteine, glutathione, and sodium borohydride at both 37° C. and 8° C. in the absence and presence of human serum to provide macromolecules capable of binding and possibly stabilizing reduced MPs. However, even these conditions failed to produce significant changes in MP spectra which would suggest stable reduction—this despite the fact that ascorbate was catalytically oxidized by the transition metal-containing MPs (Table V). The ascorbate oxidizing activity of FeTMPyP was quite pronounced followed by CuTMPyP, MnTMPyP, FeTSPP, FePPIX, and MnPPIX; MnTBAP had no oxidizing activity. Similar experiments involving incubation of MPs (5 $\mu$M) with GSH (2 mM) in 0.1 M potassium phosphate buffer, pH 7.4 and 37° C. revealed that both FeTMPyP and MnTMPyP oxidized GSH at a rate of 22 $\mu$M/min whereas the oxidation rate with CuTMPyP was 29 $\mu$M/min compared to 1.9 $\mu$M/min for non-catalyzed GSH autooxidation (not shown). Treatment of Mn and Fe porphyrins with a slight molar excess of the much stronger reductant dithionite resulted in irreversible loss of soret bands consistent with metal loss from the porphyrins.

TABLE V

| Metallo-porphyrin | Rate of Ascorbate Oxidation ($\mu$M/min) |
| --- | --- |
| none | 0.86 ± 0.03 |
| MnTBAP | 0.86 ± 0.04 |
| MnPPIX | 0.96 ± 0.05 |
| FePPIX | 1.33 ± 0.07 |
| FeTSPP | 4.58 ± 0.21 |
| MnTMPyP | 6.77 ± 0.33 |
| CuTMPyP | 6.50 ± 0.32 |
| FeTMPyP | 146.20 ± 7.2 |

Table V. Ascorbate oxidation by MPs. MPs (10 $\mu$M) were added to stirred cuvettes containing 0.1 M potassium phosphate, pH 7.4 and 50 $\mu$M ascorbate. Ascorbate oxidation was monitored at 266 nm ($\eta_m$=17,700 M$^{-1}$cm$^{-1}$). Oxidation rates (±standard errors) were determined by fitting the initial linear portion of each curve and averaging the rates (n=3).

EXAMPLE 14
Effects of Ascorbate and CTSH on Metalloporphyrin-catalyzed Nitration Yields Despite the absence of spectral changes which would indicate stable reduction of the transition metal-containing metalloporphyrins, their ascorbate and GSH oxidizing activities suggested that they did undergo cyclic reduction and reoxidation in the presence of reductants. This observation, combined with known ability of reductants like ascorbate to reduce Mn(IV) intermediates (12,13) suggested that they would be effective at inhibiting nitration catalysis by metalloporphyrins. Thus, nitration catalysis by metalloporphyrins was compared in the absence and presence of a 1.5 molar excess of ascorbate or GSH.

Figure 7:
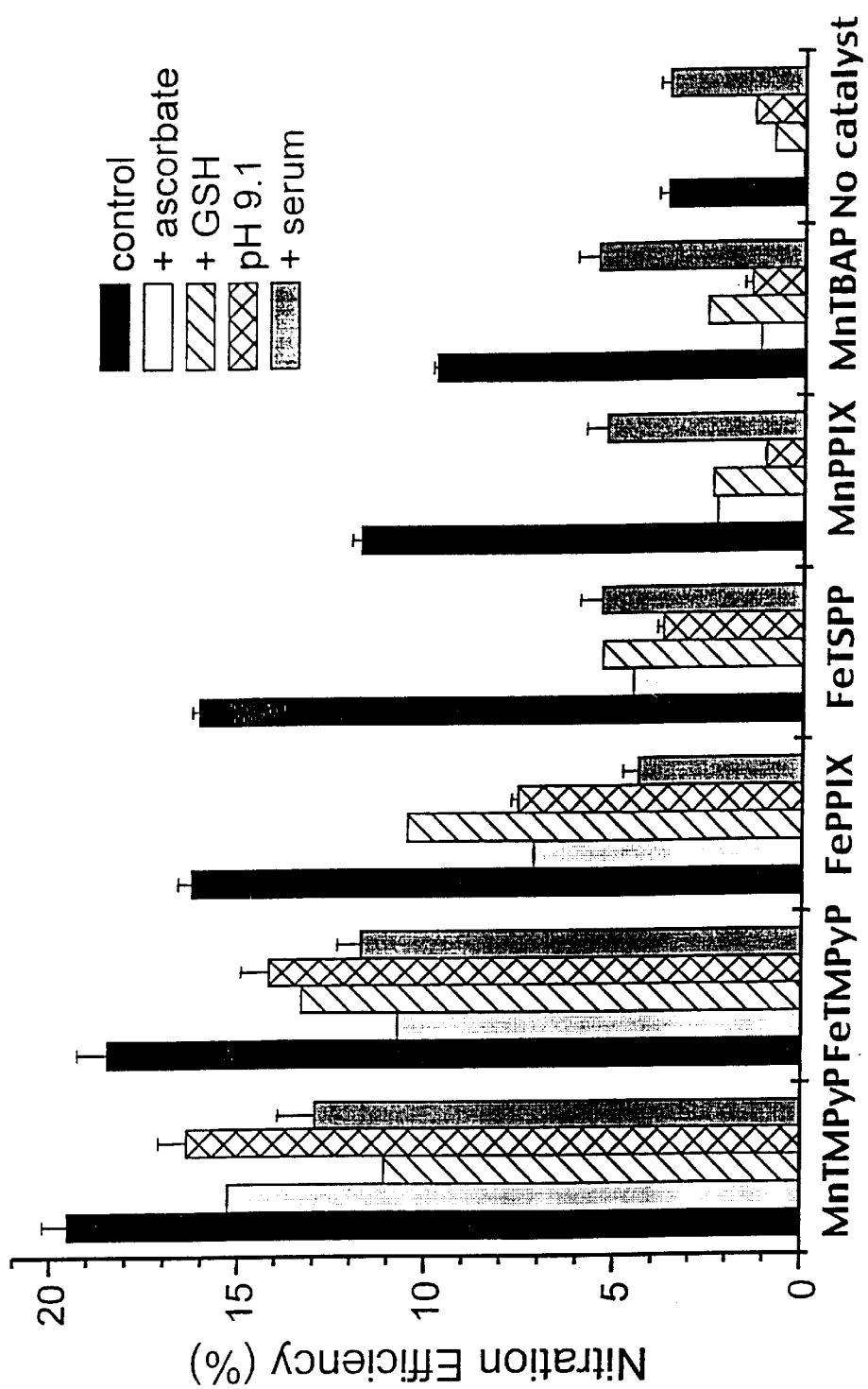
FIG. 7 shows MP-Catalyzed Nitration of HPA: effect of pH and reductants. Reaction solutions contained 8 mM hydroxyphenylacetic acid (HPA) and 10 $\mu$M of the indicated MP in 1.4 ml of 0.1 M potassium phosphate for pH 7.4 reactions and 0.1 M sodium borate for pH 9.1 reactions at 37° C. Ascorbate (150 $\mu$M), glutathione (GSH, 150 $\mu$M)) or fresh human serum were added where indicated; the final concentration of serum in the reaction represented a 1:10 dilution. Single additions of 100 $\mu$M peroxynitrite were made to reactions containing ascorbate or GSH. Three sequential additions of 100 $\mu$M peroxynitrite were made to all other reactions.

Ascorbate (150 $\mu$M) virtually eliminated non-catalyzed nitration of the tyrosine analog hydroxyphenylacetate (HPA) by peroxynitrite and had a pronounced inhibitory effect on nitration enhancement by MnTBAP and MnPPIX (FIG. 7). However, ascorbate inhibited only 35–40% of the nitration enhancement by either MnTMPyP or FeTMPyP. Ascorbate did inhibit nitration enhancement by MnTMPyP and FeTMPyP in a dose-dependent manner with complete inhibition occurring at 1.5 mM ascorbate (not shown). The inhibitory effect of ascorbate on MP-enhanced nitration was more pronounced with metalloporphyrins which possess anionic functional groups (e.g., FeTSPP, MNPPIX, and MnTBAP) suggesting that ascorbate was inhibiting via a direct interaction with the MP rather than simply reducing tyrosyl radical or nitrogen dioxide, the proposed intermediates in the nitration mechanism. Inhibition of nitration enhancement by 150 $\mu$M GSH was similar with respect to both extent and rank order (FIG. 7).

EXAMPLE 15
Effects of pH on Nitration Yields: Reaction of Metalloporphyrins with Peroxynitrite Anion Peroxynitrite anion is relatively unreactive toward biomolecules and is the predominant form at physiological pH (pK$_a$=6.8). Thus, scavengers that can react directly with peroxynitrite anion have a greater potential to inhibit its reactivity than those which scavenge only peroxynitrous acid. The efficiency of non-catalyzed nitration at pH 9.1 was 1.3% (of added peroxynitrite) compared to 3.7% at pH 7.4 (FIG. 7), consistent with nitration by peroxynitrous acid. Metalloporphyrin-mediated enhancement of nitration at pH 9.1 was utilized as an index of reaction with peroxynitrite anion. MnTBAP and MnPPIX did not enhance nitration yields at pH 9.1 as compared to non-catalyzed yields. The enhancements of nitration yields at pH 9.1 were 2.8-fold for FeTSPP, 5.7-fold for FePPIX, 10.7-fold for FeTMPyP, and 12.3-fold for MnTMPyP. Nitration enhancements by FeTMPyP and MnTMPyP at pH 9.1 were almost as great as at pH 7.4, indicating not only an efficient reaction with peroxynitrite anion but also efficient conversion of peroxynitrite anion into a nitrating species. FeTMPyP and MnTMPyP each possess four positively charged functional groups whereas all other MPs tested at pH 9.1 possess negatively charged groups (see FIG. 1). Thus, nitration enhancement by FeTMPyP and MnTMPyP is consistent with charge attraction of peroxynitrite anion.

EXAMPLE 16
Effects of Serum on Metalloporphyrin-catalyzed Nitration Yields

An attempt to characterize the MP/peroxynitrite reaction under more biologically relevant conditions was made using additions of fresh human serum to potassium phosphate buffer containing HPA as the nitration target. The addition of fresh human serum (1:10)produced no significant changes in the spectra of metalloporphyrins that might signify reduction and subsequent stabilization of the reduced forms by serum components. Addition of serum (1:10)prior to peroxynitrite had no effect on non-catalyzed nitration yields but largely eliminated the nitration enhancement by FePPIX, FeTSPP, MNPPIX, and MnTBAP (FIG. 7). Serum had much less effect on nitration yields catalyzed by FeTMPyP and MnTMPyP (FIG. 7) suggestive of a differential interaction of metalloporphyrins with some serum component. Inhibition of MP-catalyzed nitration by serum would not appear to be related to ascorbate as ascorbate completely blocked non-catalyzed nitration (FIG. 7) whereas serum had no effect.

Figure 8:
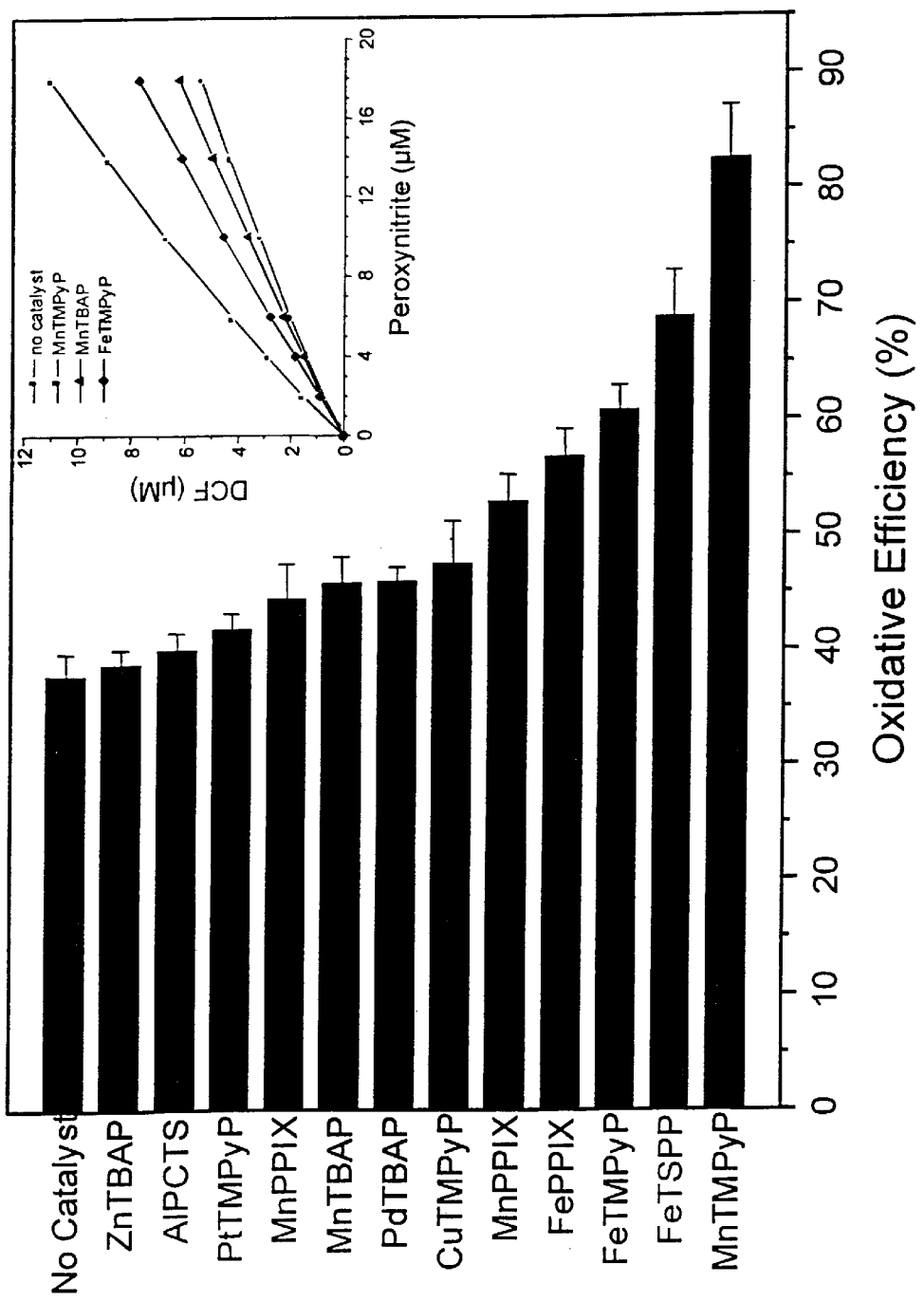
FIG. 8 shows metalloporphyrin-catalyzed oxidation of dichlorodihydrofluorescein (DCDHF). A 14.5 mM stock solution of 2,7-dichlorodihydrofluorescein was prepared as described (24). Reaction solutions were prepared in rapidly stirred glass cuvettes and contained 100 $\mu$M of DCDHF and 2 $\mu$M of the indicated MP in 1.4 ml of 0.1 M potassium phosphate, pH 7.4 at 37° C. Peroxynitrite was added sequentially to rapidly stirred cuvettes; three seperate additions of 2 $\mu$M peroxynitrite were made followed by three seperate additions of 4 $\mu$M each (see Inset). DCDHF oxidation to dichlorofluorescein (DCF) was monitored at 500 nm (59,500 $M^{-1}cm^{-1}$) (24). Oxidative efficiency was defined as the moles of DCF formed per mole of peroxynitrite added and was determined for each peroxynitrite addition. The values shown represent the average of all six additions.

EXAMPLE 17
Effect of Metalloporphyrins on Total Oxidative Yield from Peroxynitrite Dichlorodihydrofluorescein (DCDHF) undergoes a two-electron oxidation to yield the highly absorbing (and fluorescent) product dichlorofluorescein (DCF). DCDHF has been shown previously to be oxidized at an efficiency as high as 38% of added peroxynitrite (24) and was used here as an indicator to detect any changes in the total oxidative yield of peroxynitrite caused by metalloporphyrins. Metalloporphyrins caused an increase in total oxidant yield from peroxynitrite with the most pronounced effects being produced by the same four metalloporphyrins that showed the greatest nitration enhancement (FIG. 8). MnTMPyP (4 $\mu$M) increased oxidant yield by 2.2-fold to 83% of added peroxynitrite followed by the three Fe(III)-containing porphyrins. The other metalloporphyrins either had a small enhancing effect or produced no change; none were inhibitory. DCDHF oxidation was linear through six sequential additions of peroxynitrite (2 $\mu$M×3, 4 $\mu$M×3), indicating that the metalloporphyrins retained their peroxynitrite-mediated oxidative activity (FIG. 7, inset).

The metal atoms in the Cu-, Pd-, Pt-, Al-, and Zn-containing porphyrins exist in stable oxidation states and resist further oxidation under physiological conditions. In the absence of changes in redox state, these metals can function primarily as Lewis acids to stabilize reactive intermediates and, in the case of peroxynitrite, possibly to facilitate isomerization or even caged radical rearrangement to nitrate. However, with the exception of ZnTBAP, none of the non-transition metal-containing porphyrins showed any ability to accelerate peroxynitrite decomposition and had only small effects on peroxynitrite-mediated nitration.

The ability of transition metal-containing metalloporphyrins to protect against peroxynitrite-mediated injury in vivo depends primarily on three properties: 1) how fast the metalloporphyrins react with peroxynitrite anion, 2) how fast the metalloporphyrins recycle to the reduced starting compounds, and 3) how well the metalloporphyrins contain or quench the resulting reactive intermediates. Based on their respective rate constants for oxidation by peroxynitrite, Mn(III)TMPyP and Fe(III)PPIX react as fast (with peroxynitrite) as any organic compound reported to date (25,26) and significantly faster than physiologically relevant molecules like carbon dioxide (21) and cysteine (27) or metalloenzymes like Cu,Zn SOD (20), alcohol dehydrogenase (28), and aconitase (29,30) (31). True catalytic decomposition of peroxynitrite by metalloporphyrins is dependent on the presence of a reductant such as ascorbate. The co-presence of ascorbate (or other biological reductants) would appear to be critical in b o th recycling the +4 intermediate forms and in quenching reactive intermediates.

Equally important from the standpoint of scavenging peroxynitrite in vivo is the fact that (at least the cationic) Mn and Fe porphyrins react directly with the relatively stable and unreactive peroxynitrite anion ($pK_a$=6.8) (32). Thus, within a cell, relatively low concentrations of these metalloporphyrins should be capable of attracting most of the cis peroxynitrite anion (initially formed from radical-radical addition of nitric oxide and superoxide) (32)prior to its protonation and isomerization to the reactive trans peroxynitrous acid (32,34).

The ability of MnTMPyP and a Mn-porphyrin not tested here, MnTMPS (manganese [III] tetra-[3,5-disulfonatophenyl]-porphyrin), to enhance peroxynitrite-mediated nitration of the small molecular weight phenolics HPA (15) and phenol (9) has been reported previously. These earlier studies proposed that MP-catalyzed nitration occurred through a radical-mediated mechanism. This study provides additional support for a radical mechanism and extends the scope of the previous observations with regard to nitration enhancement by the Mn-porphyrins and provide new, comparative data with Fe-porphyrins. Mn- and Fe-porphyrins increase the nitration yield of both the free tyrosine analog HPA and a tripeptide containing tyrosine as the middle residue. However, it was reported recently that peroxynitrite-mediated nitration of tyrosine residues in bovine serum albumin was inhibited by iron(III)-tetra-(2,4, 6,-trimethyl-3-,3-disulfonatophenyl)-porphyrin (FeTMPS) (35). The ability of protein-bound tyrosyl residues to be nitrated by peroxynitrite in the absence but not in the presence of FeTMPS strongly suggests that the MP-catalyzed nitration mechanism requires interaction of the phenolic substrate with the metal center of the porphyrin—an interaction which would be hindered by the bulky protein. Although MP-catalyzed protein nitration was not examined directly in this study, it was noted that, following addition of peroxynitrite, re-reduction of Mn(IV) intermediates occurred relatively slowly (many seconds) in the presence of protein targets compared to the extremely rapid, cyclic re-reduction in the presence of the low molecular weight nitration targets HPA or GYA peptide. Overall these findings are consistent with a radical nitration mechanism whereby the Mn(IV) or Fe(IV)porphyrin oxidizes a low molecular weight phenolic substrate to the corresponding phenoxyl radical followed by simple addition of nitrogen dioxide radical. Indeed, the catalytic nature of the nitration reaction indicates that the phenolic substrate must be rapidly re-reducing the Mn(IV) intermediates.

A proposed mechanism for production of the nitrating species from Fe-porphyrins and inhibition by reductants is that the Fe-porphyrins appear to be capable of generating nitrating species either from the Fe(IV)=O intermediates or from the Fe(IV)–+radical cation, formed from the reaction of the intermediate Fe(IV)=O with a second peroxynitrite molecule (14). However, both oxidized iron intermediates are capable of being rapidly reduced by ascorbate or other intracellular reductants such that Fe(IV)–+is unlikely to exist in vivo. Thus, in the presence of intracellular reductants, the nitration mechanism will be interrupted and Fe-porphyrins should catalyze peroxynitrite decomposition as described for MnTMPyP.

Ascorbate and GSH virtually eliminated non-catalyzed nitration by peroxynitrite whereas serum had no effect. However, serum was effective at inhibiting MP-catalyzed nitration, suggesting that some MP/serum interaction unrelated to antioxidants. At the same concentrations which eliminated non-catalyzed nitration, ascorbate and GSH largely prevented the enhancement of nitration by MnTBAP, MnPPIX, and FeTSPP but had much less inhibitory effect on the nitration enhancement by FePPIX, FeTMPyP, and MnTMPyP. Complete inhibition of nitration enhancement by these latter three MPs required a 10-fold higher concentration of ascorbate.

Thus, it is reasonable to propose that ascorbate inhibits nitration by one or more of three mechanisms: 1) by reducing the Mn(IV) or Fe(IV) intermediate thereby preventing it from oxidizing the phenolic substrate, 2) by reducing the tyrosyl radical back to the parent tyrosine, and/or 3) by reducing nitrogen dioxide to nitrite. If ascorbate inhibited nitration solely by reducing phenoxyl radical and/or nitrogen dioxide, then the extent of inhibition should be similar regardless of which metalloporphyrin catalyzed the reaction. Thus, it would appear that ascorbate inhibition of nitration is primarily due to its direct reduction of the intermediate +4 forms. The fact that FePPIX-, FeTMPyP-, and MnTMPyP-catalyzed nitration is more resistant to inhibition by ascorbate suggests that their respective +4 forms interact less well with ascorbate. In any event, it is apparent that these three metalloporphyrins are the most efficient at increasing the yield of reactive intermediates from peroxynitrite, possibly due to their more efficient reaction with peroxynitrite anion (FIG. 7).

MnTMPyP has been reported to exist in the Mn(II) state inside bacterial cells apparently due to the ability of macromolecules to bind and stabilize the Mn(II) form of MnTMPyP (22). Similar color changes (reddish brown to green) consistent with intracellular formation of Mn(II) forms of MnTMPyP and MnTBAP have been observed in primary cultures of rat motor neurons (23). However, no significant changes in metalloporphyrin spectra were seen in vitro which would suggest that Mn(III)- or Fe(III)-porphyrins could exist in stable reduced states (Mn[II] or Fe[II]) at ambient oxygen concentrations despite many different experimental conditions, including cooling to 8° C. and the addition of effective reductants both in the absence or presence of serum. Further study is needed to determine the conditions and/or cellular components needed to obtain stable reduced forms of Mn- and Fe-porphyrins.

The possibility that stable +2 oxidation states of Mn and Fe porphyrins may exist intracellularly has important implications for these compounds as peroxynitrite detoxifiers, i.e., compounds capable of both scavenging and harmlessly decomposing peroxynitrite. Mn[II] or Fe[II] forms of porphyrins should be capable of carrying out complete two-electron reductions of peroxynitrite to yield hydroxide anion, nitrite, and Mn(IV) or Fe(IV) intermediates which could then be rapidly reduced to Mn(III) and Fe(III) forms by reductants like ascorbate, followed by slow reduction to cell-stabilized Mn(II) or Fe(II) forms in preparation for another catalytic cycle. Thus, in theory, Mn(II)- or Fe(II)-porphyrins could act as catalytic peroxynitrite reductants without initiating other deleterious oxidative reactions. Protective effects of Mn(III) and Fe(III)porphyrins in cells (6,22,35) and in whole animals (36) may well have resulted from the formation of Mn(II) and Fe(II) forms, although their formation was not demonstrated.

FeTSPP, FePPIX, and MnTBAP react with peroxynitrite more slowly than does FeTMPyP. However, these metalloporphyrins might be more efficacious than FeTMPyP at preventing peroxynitrite-mediated injury in vivo since cellular antioxidants virtually eliminated their nitration enhancing activities. Also, FeTSPP, FePPIX, and MnTBAP had much less ascorbate oxidizing activity and thus, would have less potential to deplete cellular antioxidants as compared to FeTMPyP. The ascorbate oxidizing activity of FeTMPyP, in and of itself, would suggest an inherent cytotoxic potential for this compound not only from the standpoint of ascorbate depletion but also due to subsequent superoxide generation as Fe(II)TMPyP rapidly autooxidizes back to Fe(III)TMPyP. While two recent studies focused on the ability of FeTMPyP to protect against peroxynitrite-mediated injury, neither reported any toxicity related to FeTMPyP itself. However, the duration of cell or whole animal exposure to FeTMPyP was limited to only a few hours (34,35). Further studies are needed to establish whether FeTMPyP depletes ascorbate in cells and/or whether it is stabilized by binding macromolecules as MnTMPyP appears to be (22).

The relatively high nitration and peroxynitrite decomposing activities of heme (FePPIX) suggest that some endogenous heme protein(s) may function to scavenge peroxynitrite and/or enhance its pathologic reactivity. The iron in hemoglobin is relatively unreactive toward peroxynitrite (37), presumably due to the additional iron ligands that modify its redox properties and sterically hinder access of peroxynitrite to the iron. However, free heme is present in cells and is a prosthetic group of many other hemoproteins.

It is interesting to note that myeloperoxidase, the first mammalian heme protein shown to react rapidly with peroxynitrite, actually enhances the nitration yield (38,39) similar to the isolated Fe porphyrins.

The Mn- and Fe-porphyrins are planar molecules with their functional groups extending outward (FIG. 1). The functional groups affect not only the redox activity of the central metal atom but also determine how the metalloporphyrins will physically interact with other biomolecules. Thus, overall effects of metalloporphyrins on the redox environment of the cell may depend quite significantly on the nature of these functional groups. For example, it appears that metalloporphyrins possessing anionic functional groups (e.g. MnTBAP, MnPPIX, and FeTSPP) react poorly if at all with peroxynitrite anion—a property that could severely limit their effectiveness as scavengers. On the other hand, the metalloporphyrins possessing cationic groups (MnTMPyP or FeTMPyP) have been reported to bind both DNA and RNA (40,41). The ability of the TMPyP porphyrins to bind nucleic acids and enhance peroxynitrite reactivity could have the effect of directing oxidation to DNA—a particularly harmful prospect that could limit their usefulness as well. Toxicities associated with discreet subcellular localization could be circumvented by altering the size and charge of functional groups or by coupling the metalloporphyrins to other compounds which would favor localization to desired or non-critical sites in the cell (42).

The concept of a compound acting catalytically to decompose peroxynitrite to innocuous nitrate is considerably more appealing than that of a sacrificial antioxidant such as a thiol-based scavenger. Recently Lee et al. (12) reported that superoxide could act as the reductant for Mn(IV)=O formed from the reaction with peroxynitrite resulting in a superoxide coupled peroxynitrite reductase. The results of Lee et al. offer the tantalizing possibility that Mn(III)porphyrins could function simultaneously as both a superoxide 'oxidase' and a peroxynitrite 'reductase' within on e catalytic cycle. However, a simple comparison of the relative rate constants for superoxide and ascorbate reacting with Mn(IV)TMPyP and their relative in vivo concentrations strongly suggests that ascorbate would be the more likely catalytic reductant.

Mn-porphyrins that have been shown to protect against oxidative injury in cells react relatively slowly with superoxide, making it difficult to explain their effects based on dismuting activity alone. Both oxidized and reduced forms of Cu,Zn SOD react with superoxide at $2 \times 10^9$ $M^{-1}s^{-1}$ (43). The fastest rate yet reported for superoxide reacting with a Mn(II)porphyrin, the suspected intracellular form, is $2.2 \times 10^8$ $M^{-1}s^{-1}$ for the octabromo derivative of MnTMPyP, termed MnOBTMPyP (5). Superoxide reaction rates are much slower for Mn(III)OBTMPyP and for all other Mn porphyrins tested to date. Even for Mn(II)OBTMPyP, a concentration of 90 $\mu$M would be needed to provide the same level of dismuting activity as is provided by endogenous levels of SOD1. On the other hand, many of the Mn- and Fe-porphyrins react with peroxynitrite at rates which are faster than peroxynitrite reacts with any known biomolecules. Thus, low micromolar amounts of metalloporphyrins could effectively prevent peroxynitrite-mediated oxidation of biomolecules present at much higher concentrations. Indeed, it is arguable that peroxynitrite scavenging has been the basis for much of the protective effects of the Mn-porphyrins in various model systems which has been attributed to SOD activity. In any case, a strong rationale exists for use of Mn- and Fe-porphyrins as peroxynitrite scavengers provided the potential toxicological properties can be identified and thereby minimized.

A rapid reaction of the porphyrin with peroxynitrite does not necessarily mean that peroxynitrite will be safely decomposed. In fact, under the experimental conditions used (pure solutions of porphyrin, peroxynitrite, and oxidizable target), the Mn and Fe porphyrins typically increased the overall reactivity of peroxynitrite rather than diminishing it. Paradoxically, many of these compounds have been shown to prevent oxidative injury in vivo. These apparent discrepancies are reconciled by proposing that Mn(IV) or Fe(IV) intermediates are needed to enhance peroxynitrite reactivity and that they are rapidly and harmlessly detoxified (via reduction to [III] states) in vivo by cellular antioxidants such as ascorbate.

Some Mn and Fe porphyrins possess the ability to catalytically decompose peroxynitrite and that this property could explain much, if not all, of the protective effect that these compounds have shown in various cell culture and animal models. However, because these compounds were first introduced as low molecular weight superoxide dismutase mimetics, this moniker has stuck and many investigators still regard them as SOD mimics despite the fact that this activity is too low to account for their biological effects.

One of the fundamental differences (and perhaps the most important) between the Mn and Fe porphyrins is fact that the latter can catalytically decompose peroxynitrite even in the absence of reductants such as ascorbate or glutathione (GSH). Some of the Mn porphyrins react even faster with peroxynitrite ($\sim 2\times 10^7$ $M^{-1}s^{-1}$) than the Fe porphyrins ($\sim 3\times 10^6$ $M^{-1}s^{-1}$). However, in the absence of reductants, the Mn(III)porphyrins are oxidized to their respective Mn(IV) forms and cease to decompose peroxynitrite, i.e., they can decompose only one molar equivalent of peroxynitrite. The Fe(III) porphyrins, on the other hand, appear to be oxidized to Fe(IV) by the first molecule of peroxynitrite, then to the Fe(V)-radical cation by a second peroxynitrite. Fe(V)-oxidizes a third molecule of peroxynitrite to regenerate the Fe(IV) compound and can then cycle between Fe(V)- and Fe(IV), alternately oxidizing and reducing peroxynitrite. This peculiar catalytic mechanism of the Fe porphyrins may be an in vitro phenomenon that would never occur in cells where antioxidants like ascorbate are plentiful.

An additional confounding aspect of the chemistry of the Mn and Fe porphyrins is that they can be readily reduced to the +2 oxidation state by reductants like ascorbate and GSH. At ambient oxygen (~250 EM), the reoxidation to the +3 state is quite rapid, resulting in a net production of superoxide. However, the +2 state appears to considerably more stable within cells, for reasons which are presently unknown. The end result of a stable +2 form of Mn and Fe porphyrins is that they could, theoretically, carry o u t complete, two-electron reduction of peroxynitrite, making them more efficient scavengers.

The present invention provides evidence to support the use of iron(III)porphyrins, especially iron(III)) meso 5,10, 15,20-tetrakis-(4-carboxy)-phenyl porphyrin (FeTCPP) and iron(III)) meso 5,10,15,20-tetrakis-(4-carboxymethyl)-phenyl porphyrin (FeTMeO-TCPP) as a therapy for Amyotrophic Lateral Sclerosis and other neurodegenerative diseases involving motor neuron death. More specifically, the present invention demonstrates: 1) in vitro evaluation of FeTCPP as a peroxynitrite scavenger, nitration catalyst, and ascorbate oxidase, 2) use of FeTCPP and FeTMeO-TCPP in primary cultures of rat motor neurons to determine ability to protect from growth factor withdrawal (conditions known to cause peroxynitrite-mediated apoptotic cell death), and 3) evaluation of FeTCPP and FeTMeO-TCPP in ALS-SOD (G93A) transgenic mice to determine ability to prolong lifespan of mice approaching end-stage motor neuron death (progressive paralysis).

EXAMPLE 18

Methodological Details of Cultured Motor Neuron Experiments

Culture Motor neurons were prepared from embryonic day 15 (E15) rat spinal cords by a combination of metrizamide gradient centrifugation and immunopanning with the monoclonal antibody IgG192 (Chandler et al., *J. Biol. Chem.* 259:6882–6889, 1984) as previously described (Estevez et al., *J Neurosci* 18:923–931, 1998; Henderson C E, Bloch-Gallego E, Camu W (1995): Purification and culture of embryonic motorneurons. In Cohen J, Wilkin G (eds): Neural Cell Culture: A Practical Approach. Oxford, England: IRL Press, pp 69–81). Long-term cultures of motor neurons were performed as described by Pennica et al. (Pennica et al., *Neuron* 17:63–74, 1996). Briefly, motor neurons were plated at a density of 200 cells/cm2 on 35 mm dishes precoated with polyornithine-laminin in Neurobasal medium supplemented with B27 (Life Technologies, Grand Island, N.Y.), 2% horse serum, 0.5 mM L-glutamine, 25 μM 2-mercaptoethanol and 25 μM L-glutamate. Every 3–4 days ¾ of the culture medium was replaced by fresh medium lacking L-glutamate and containing sufficient quantities of BDNF or FeTCPP to supplement the 2 ml of medium in the dish. More than 94% of the cells were immunoreactive for the p75 low-affinity neurotrophic receptor ($p_7$5NTR) and Islet ½, which are markers for motor neurons. The experiments were repeated at least 2 times using the same lot of Neurobasal medium and B 27 supplement.

The number of motor neurons with neurites longer than 4 soma diameters present in parallel cultures treated with BDNF at a final concentration of 100 pg/ml 24 h after plating or culture media replacement was considered 100% motor neuron survival. FeTCPP was resuspended in complete Neurobasal medium at a 5 mM concentration. Dilutions were performed of the stock solution to add 20 μl per dish.

EXAMPLE 19

Catalysis of Peroxynitrite-Mediated Nitration by FeTCPP and Catalytic Ascorbate Oxidation Several Mn and Fe porphyrins catalyze phenolic nitration by peroxynitrite. The average efficiency of nitration catalysis by FeTCPP was 22.7%, making it comparable to the highest nitration catalyst shown in the figure (FeTSPP). Concentrations of ascorbate in vivo would readily inhibit nitration catalysis by FeTCPP, so these data are mainly intended as a comparison to other Fe and Mn porphyrins and not as potential toxicological properties. FeTCPP catalytically oxidizes ascorbate at a rate of 5.8 μM/min. Thus, FeTCPP is considerably less reactive toward ascorbate than are other Fe porphyrins; this property would have considerably more toxicological relevance from the standpoint of depleting cellular ascorbate and concomitant production of superoxide upon reoxidation to Fe(III).

EXAMPLE 20

Figure 9:
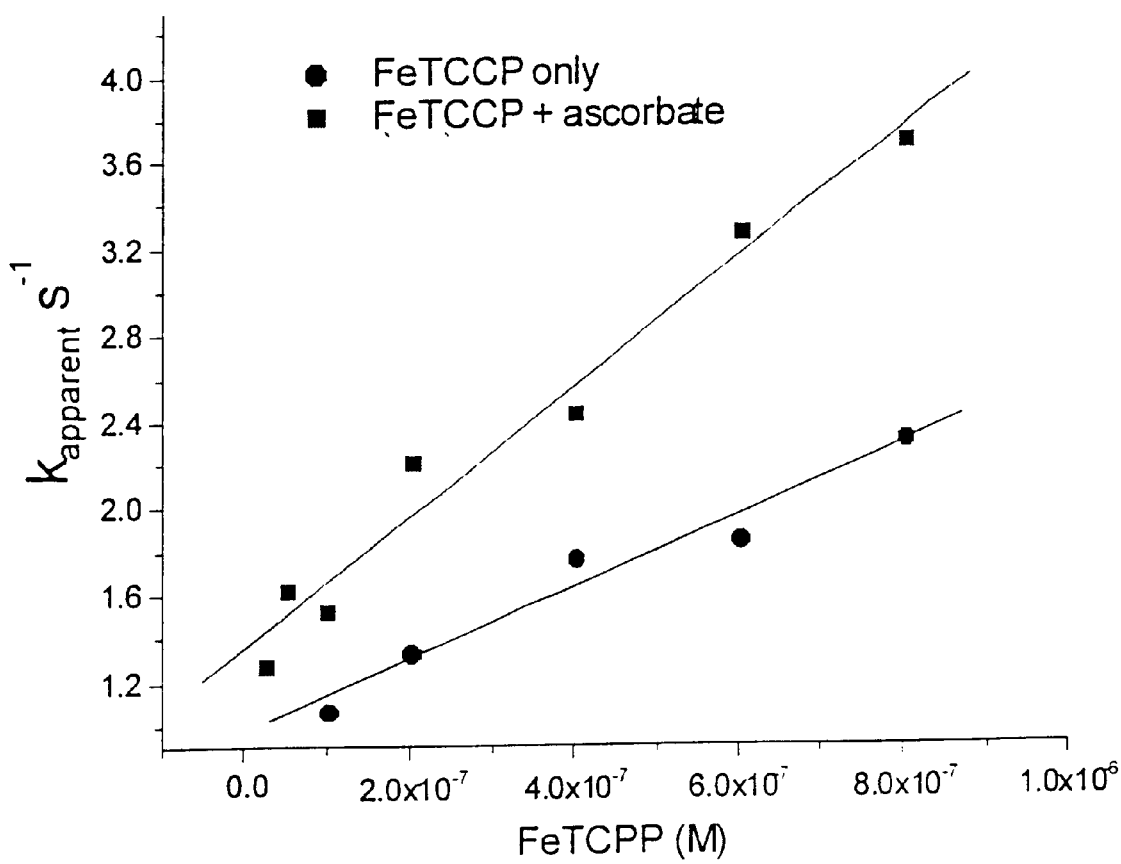
FIG. 9 shows a determination of rate constant for FeTCPP-catalyzed decomposition of peroxynitrite. Reactions contained the indicated concentration of FeTCPPin 1.4 ml of 0.1 M potassium phosphate, pH 7.4 in the absence or presence to 150 $\mu$M ascorbic acid. Peroxynitrite (100 $\mu$M) was added to rapidly stirred cuvettes at 37° C. and the decay of peroxynitrite was monitored continuously at 302 nm. Decay data were fitted to the equation describing first order decay to obtain apparent decay rates ($k_{apparent} sec^{-1}$). Apparent decay rates as a function of FeTCPP were fitted by linear regression and the rate constant was obtained slope of the line. The rate constant for FeTCPP-catalyzed peroxynitrite decomposition was $1.6 \times 10^6$ $M^{-1}s^{-1}$ in the absence of ascorbate and increased to $2.9 \times 10^6$ $M^{-1}s^{-1}$ when ascorbate was added. The increase in rate is consistent.

FeTCPP Catalytically Decomposes Peroxynitrite even in the Absence of Added Reductant Submicromolar concentrations of FeTCPP accelerated the decomposition of 100 μM of peroxynitrite when peroxynitrite was added (bolus) to rapidly stirred solutions at 37° C. (FIG. 1). Linear regression of apparent rates for peroxynitrite decay at different FeTCPP concentrations gave an estimated rate constant of $1.6\times 10^6$ $M^{-1}s^{-1}$ (FIG. 9). Addition of ascorbic acid immediately prior to peroxynitrite, increased the rate constant less than two-fold to $2.9 \times 10^6$ $M^{-1}s^{-1}$. This indicates that reduction of the Fe(IV)-radical cation) intermediate is not rate-limiting to peroxynitrite decomposition. Such reductant-independent catalytic decomposition of peroxynitrite represents a fundamental difference between Fe porphyrins and their Mn-containing counterparts.

Figure 10A:
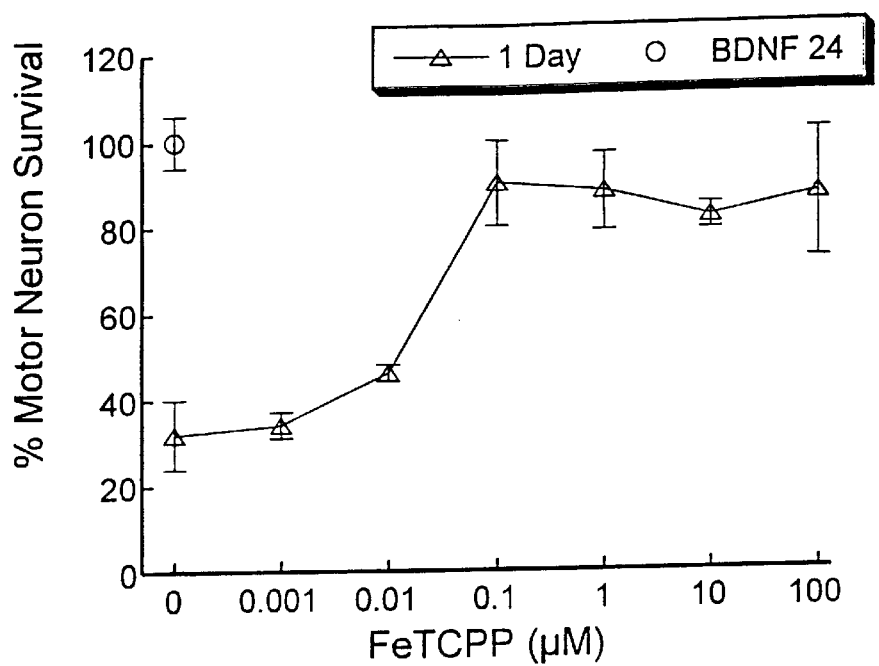
FIG. 10 shows a dose-response for 24 hour (FIG. 10A) and 72 hour (FIG. 10B) protection of cultured motor neurons by FeTCPP.
Figure 10B:
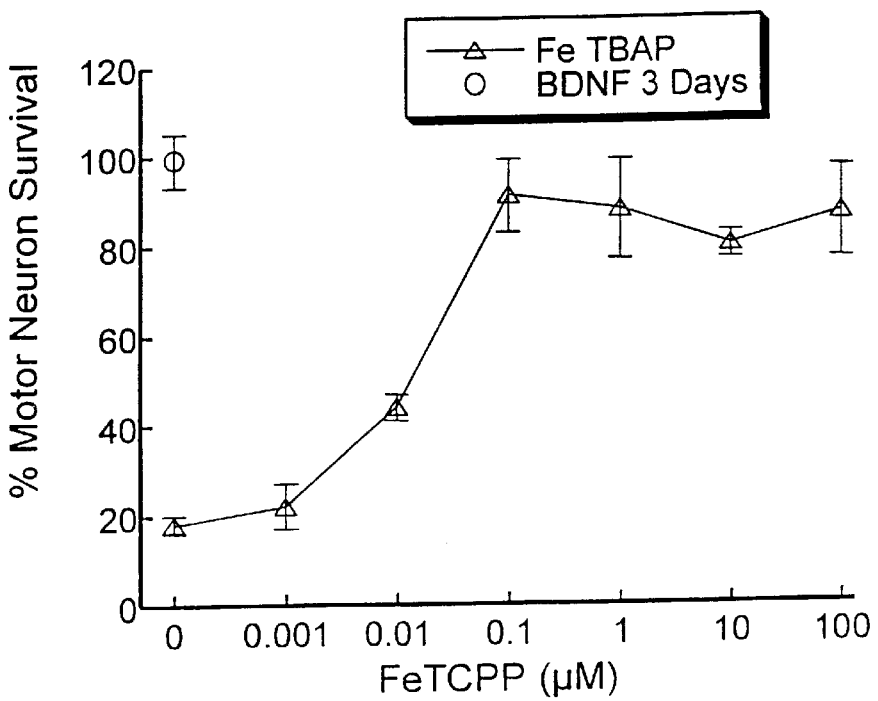
Figure 11:
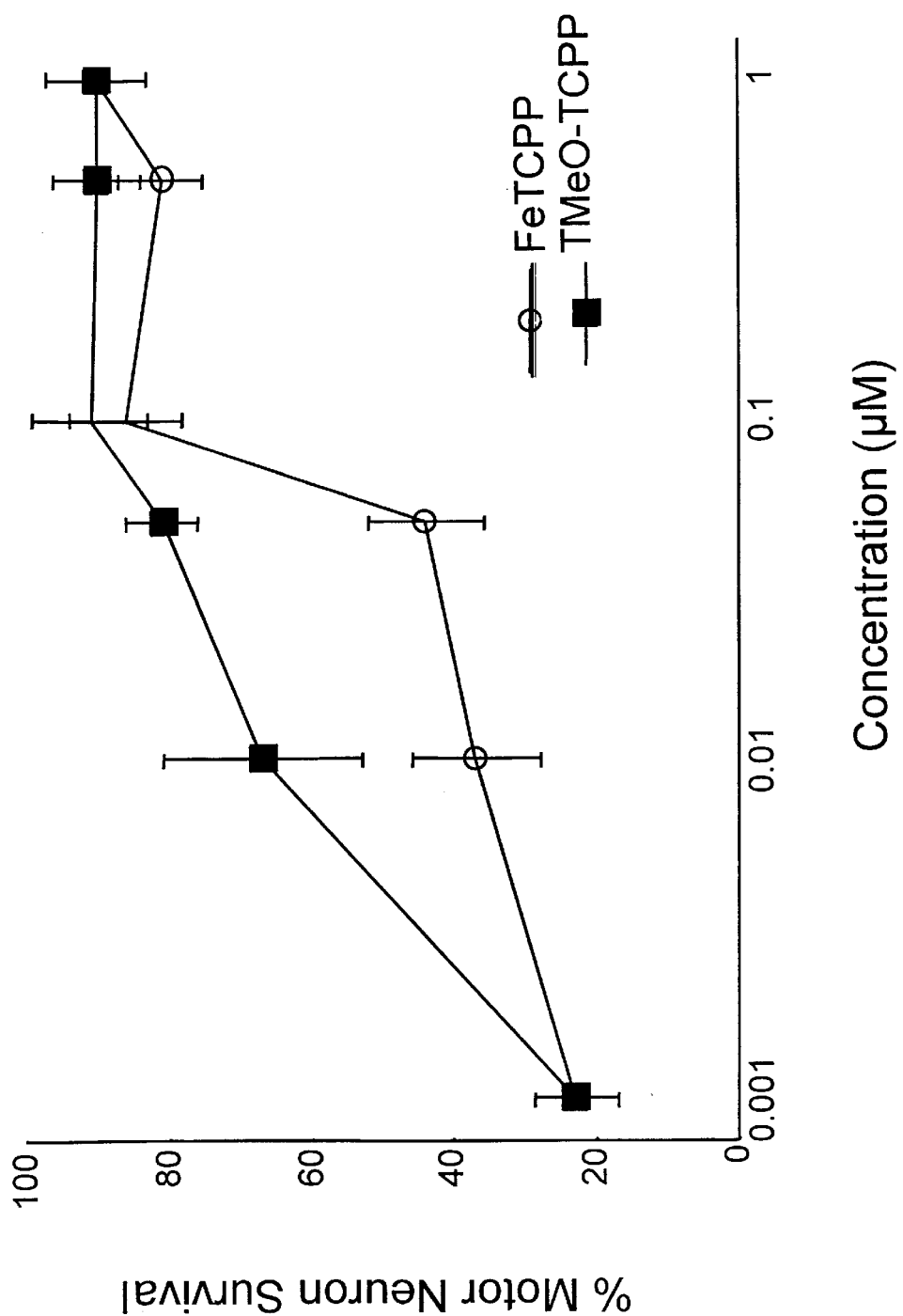
FIG. 11 shows a comparison of dose-response for 72 hour protection of cultured motor neurons by FeTCPP and TMeO-FeTCPP.

EXAMPLE 21
FeTCPP and FeTMeO-TCPP Protect Cultured Motor Neurons from Growth Factor Withdrawal at Remarkably Low Doses Rat motor neurons survive many days in culture when brain-derived neurotrophic factor (BDNF) is added to the culture media. Because motor neurons are the cells that preferentially die in ALS, primary cultures of motor neurons represent the best non-animal model of ALS. Withdrawal of BDNF results in apoptotic death of >70% of motor neurons within 24 h. Cell death was correlated with expression of the neuronal form of nitric oxide synthase (nNOS) and the production of peroxynitrite, as evidenced by protein tyrosine nitration. When FeTCPP is added to the culture media in place of BDNF and motor neuron survival is assessed at 24 h, some protection is seen at concentrations as low as 0.01 $\mu M$ (FIG. 10A). Maximal cell survival of 90% is seen at 0.1 $\mu M$ and remains at 90% at a concentration of 100 $\mu M$ FeTCPP, indicating that even relatively high concentrations are not toxic. The dose-response for FeTCPP-mediated survival of motor neurons at 72 h is virtually identical to the 24 h survival results (FIG. 10B). Additionally, a comparison of the effect of FETCPP and its tetra-methyl ester derivative, TMeO-FeTCPP, on motor neuron survival at 72 hr. (FIG. 11) after trophic factor deprivation demonstrates that TMeO-FeTCPP provides twice the level of protection at low concentrations, 0.01 $\mu M$, and a slightly greater level of protection over FeTCPP at a concentration of 0.1 $\mu M$.

Figure 12:
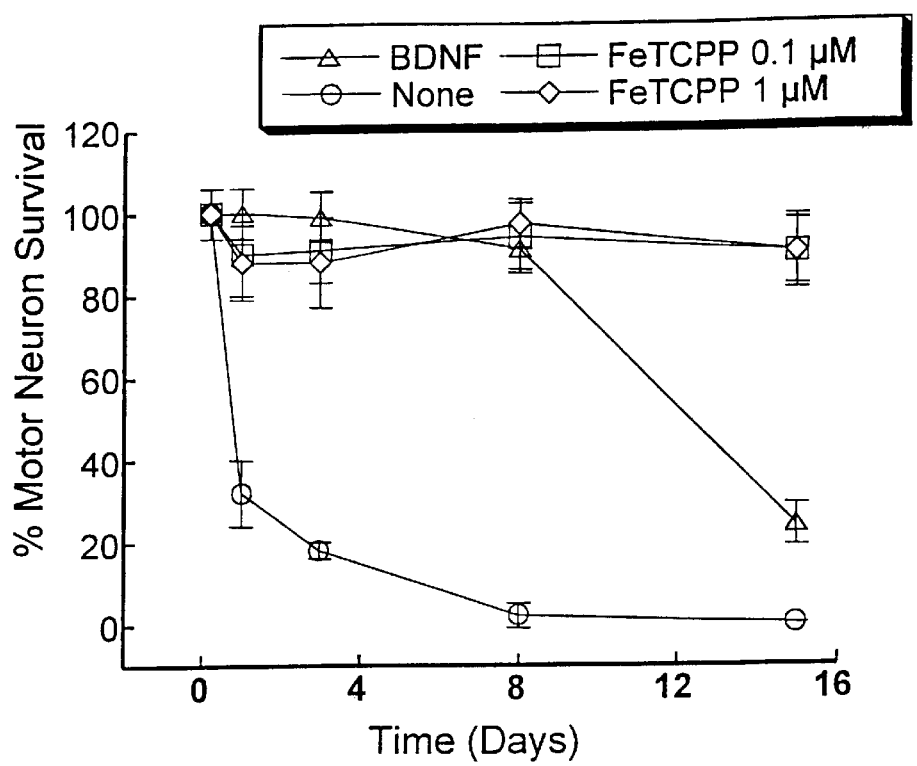
FIG. 12 shows a long-term protective effect of FeTCCP on Cultured Motor Neurons.

Assessment of long-term motor neuron survival at two doses of FeTCPP (0.1 $\mu M$ and 1.0 $\mu M$) reveal that FeTCPP is as effective as BDNF. Between day 8 and day 16, most of the motor neurons (80%) die even in the presence of BDNF (FIG. 12). Remarkably, even the lower dose of FeTCPP maintains 90% cell survival at day 16 suggesting that FeTCPP is even more effective than the natural growth factor (FIG. 12). These data also suggest that FeTCPP may have multiple mechanisms of action, some of which are related to detoxification of peroxynitrite and some that are peroxynitrite-independent.

Figure 13A:
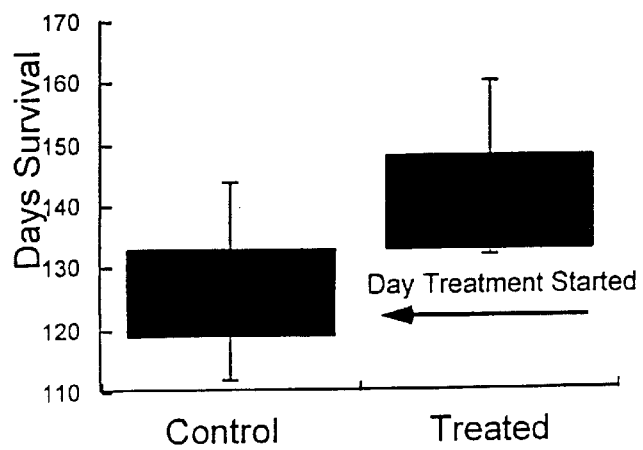
FIG. 13A: Transgenic mice (n=9) were injected intraperitoneally with 3 mg/kg/day of a low molecular weight (844.6) synthetic iron porphyrin. Treatment began essentially at the onset of symptoms (two mice displayed foot dragging and others showed signs of hind limb weakness). Treatment was continued until such time that signs of diaphragm weakness (labored breathing) necessitated sacrifice. A control group of transgenic mice was treated with vehicle only (phosphate-buffered saline).

EXAMPLE 22
FeTCPP and FeTMeO-TCPP Substantially Prolongs Lifespan of ALS-SOD1 (G93A) Transgenic Mice Mice transgenic for the G93A mutated form of SOD1 are generally accepted as the standard model of motor neuron disease. Compounds which have been shown to be effective in G93A mice have proved to be similarly effective in human ALS patients. A group of G93A was treated with 5 mg/kg of FeTCPP-an iron(III) porphyrin that was found to be a very effective peroxynitrite decomposition catalyst in vitro. This compound extended the mean survival time by 13 days (from 127 to 140 days) (FIG. 13A).

Figure 13B:
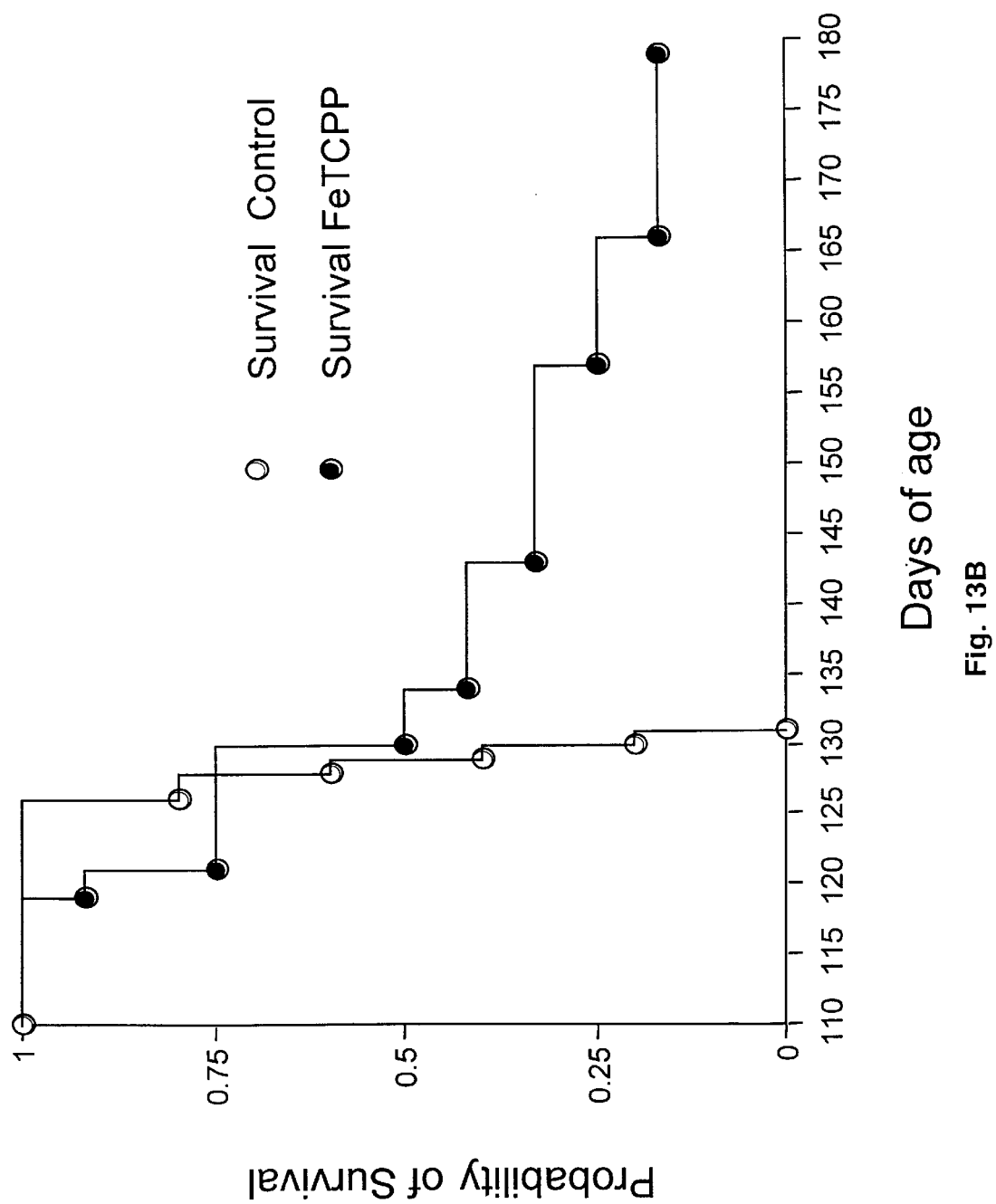
FIG. 13B: Transgenic mice were injected intraperitoneally with 1 mg/kg/day of a low molecular weight (844.6) synthetic iron porphyrin. Treatment began at day 60 prior to the onset of symptoms. A control group of transgenic mice was treated with vehicle only (phosphate-buffered saline).

A significantly enhanced survival effect occurs when FeTCPP is initially administered prior to onset of paralysis (FIG. 13B). A group of G93A mice was treated with 1 mg/kg of FeTCPP intraperitoneally beginning at 60 days of age. As with the control group in FIG. 13A, none of the control group in this test survived past 132 days. However, the probability of survival at 140 days was about 37% and at approximately 180 days survival was still at 20%. Administration of a significantly lower dose of FeTCPP prior to onset of symptoms extended the survival time beyond the upper limit of about 148 days when FeTCPP was administered at the onset of symptoms.

The only drug available in the U.S. for ALS patients, Rilutek® (riluzole), extended lifespan by only about 7 days in these mice. Equally significant was the fact that this compound extended lifespan even though treatment was initiated at the time of onset of symptoms. Virtually all compounds tested in this model system to date have been administered for the entire life of the animal. Not only is FeCPPT more effective at lower doses than anything previously reported, it prolongs lifespan even if treatment is initiated after onset of the disease. This is particularly significant since treatment of human disease would, necessarily, begin only after diagnosis.

Both FeTCPP and FeTMeO-TCPP slow the progression of motor neuron death in mice which contain a human transgene (G93A mutant of Cu,Zn superoxide dismutase) known to cause ALS. FeTCPP and FeTMeO-TCPP also prolong survival of cultured motor neurons deprive of normal growth factors. Additionally, FeTCPP protects isolated hearts from the injurious effects of ischemia and reperfusion. FeTCPP may be useful in models of spinal cord injury. In all of these conditions, oxidative injury, possible mediated by peroxynitrite, is a common theme. However, the remarkable ability of FeTCPP to essentially substitute for peptide growth factors in cultured motor neurons suggests other, novel properties that may have much wider applicability. Therefore, FeTCPP and FeTMeO-TCPP would be potential candidates for treatment for neurodegenerative disease in humans and as a component of a preservation solution for donor organs.

Several groups are attempting to synthesize and characterize compounds which can specifically scavenge the biological oxidant peroxynitrite, either in a sacrificial or catalytic manner. (Catalytic scavenging would, at least in theory, greatly lower the dose of drug needed for a therapeutic effect.) Because peroxynitrite has been implicated in many, diverse human disease conditions, such a drug would have wide applicability. At present, no such catalytic peroxynitrite scavenger exists, although the iron and manganese porphyrins, as a general class, represent the best candidates to date. Compounds such as N-acetylcysteine (NAC) or glutathione (GSH) esters are simple sulfhydryl-based antioxidants that sacrificially scavenge peroxynitrite. However, because such compounds react relatively slowly with peroxynitrite and are consumed in the reaction, very large concentrations (doses) are needed, thereby limiting their efficacy and therapeutic/toxic ratio (therapeutic index). Selenium-based compounds such as Ebselen and selenomethionine react quite fast with peroxynitrite and can be recycled (following reaction with peroxynitrite) by sulfhydryl antioxidants in cells. However, metabolism of these compounds releases the selenium atom that, as free selenium, is highly toxic.

FeTCPP is very water soluble but retains sufficient lipid solubility to readily cross cell membranes and the blood-brain-barrier. Thus, no limitations appear to exist with regard to delivery of the compound to the relevant tissues. FeTCPP, like other Fe (and Mn)porphyrins, has several, distinct chemical properties related to their ability to undergo cyclic oxidation and reduction as well as to bind macromolecules via their side chain functional groups. At least one mechanism for their protective effects in cells and animals is via catalytic scavenging of peroxynitrite.

The following references were cited herein:
1. Kadish, K. M. and Larson, G. (1977). *Bioinorg. Chem.* 7:95–105.
2. Halliwell, et al., (1978). *Biochem. Soc. Trans.* 6:1342–1343.
3. Pasternack, et al., (1979). *J. Inorg. Biochem.* 11:261–267.
4. Peretz, et al., (1982). *Internat. J. Rad. Biol. & Red. Stud. Physics, Chem. &. Med.* 42:449–456.
5. Batinic-Haberle, et al., (1997). *Arch. Biochem. Biophys.* 343:225–233.
6. Day, et al., (1997). *Arch. Biochem. Biophys.* 347:256–262.
7. Stern, et al., (1996). *J. Am. Chem. Soc.* 118, 8735–8736
8. Marla, et al., (1997). *Proc. Nat. Acad. Sci.* (USA) 94:14243–14248.
9. Balavoine, et al., (1997). *Nitric Oxide.* 1:507–521.
10. Sies, et al., (1997). *J. Biol. Chem.* 272:27812–27817.
11. Beckman, et al., (1996). *Amer. J. Physiol. Cell Physiol.* 40:(5)C1424–C1437
12. Lee, et al., (1998). *J. Am. Chem. Soc.* 120:6053–6061.
13. Lee, et al., (1997). *Bioorg. &. Med. Chem. Lett.* 7:2913–2918.
14. Lee, et al., (1998). *J. Am. Chem. Soc.* 120:7493–7501.
15. Groves, J. T.; Marla, S. S. *J. Am. Chem. Soc.* 1995, 117, 9578.
16. Ferrer-Sueta, et al., (1997). *Chem. Res. Tox.* 10:1338–1344.
17. Beckman, et al., (1994). *Meth. Enzymol.* 233:229–240.
18. Hughes, M. N. and H. G. Nicklin. (1968) *J. Chem. Soc.* (A) 450–452.
19. Crow, et al., (1996). *Meth. Enzymol.* 269:185–194.
20. Ischiropoulos, et al., (1992) *Arch. Biochem. Biophys.* 298:431–437.
21. Lymar, et al., (1996). *Biochemistry* 35:7855–7861.
22. Liochev, et al., (1995). *Arch. Biochem. Biophys.* 321:271–275.
23. Estevez, et al., (1998) *J. Neurosci.* 18:923–931.
24. Crow, J. P. (1997). *Nitric Oxidem* 1, 145–157.
25. Masumoto, et al., 1996. *FEBS Lett.* 398:(2–3)179–182.
25. Padmaja, et al., (1996). *Free Rad. Biol. Med.* 21:(3) 317–322.
27. Radi, et al., (1991). *J. Biol. Chem.* 266:4244–4250.
28. Crow, et al., (1995). *Biochemistry* 34:3544–3552.
29. Hausladen, et al., (1994). *J. Biol. Chem.* 269:29405–29408.
30. Castro, et al., (1994). *J. Biol. Chem.* 269:29409–29415.
31. Arteel, et al., (1999). *FEBS Letters* 445:226–230.
32. Beckman, et al., (1990). *Proc. Nat. Acad. Sci.* (USA) 87:1620–1624.
33. Huie, et al., (1993). *Free Rad. Res. Comm.* 18:195–199.
34. Crow, et al., (1994). *Free Rad. Biol. Med.* 16:331–338.
35. Misko, et al., (1998). *J. Biol. Chem.* 273:15646–15653.
36. Salvemini, et al., (1998). *Proc. Nat. Acad. Sci.* (USA). 95:2659–2663.
37. Alayash, et al., (1998). *Arch. Biochem. Biophys.* 349:65–73.
38. Floris, et al., (1993). *Eur. J. Biochem.* 215:767–775.
39. Sampson, et al., (1996). *Meth. Enzymol.* 269:210–218.
40. Pasternack, et al., (1983). *Biochemistry* 22:2406–2414.
41. Ward, et al., (1986). *Biochemistry* 25:7827–7833.
42. Hunt, et al., (1997). *Chemistry & Biology* 4:845–858.
43. Forman, et al., (1973 *Arch. Biochem. Biophys.* 158:396–400.
44. Prutz, et al., (1985). *Arch. Biochem. Biophys.* 243:125–134.
45. Imam, et al., (1999). *Brain Research* 837:15–21.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A compound of the formula

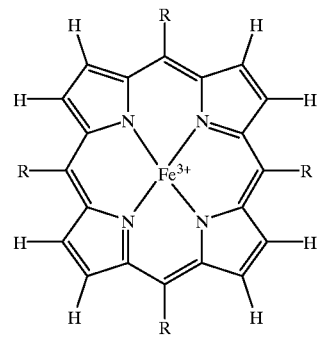

wherein R is selected from the group consisting of $(C_6H_4)$ $(3,5-OH)_2$, $(C_6H_4)CH_2OH$, $(C_6H_4)PO_3H$, $(C_6H_4)(3-NO_2-4-OH)$, $(C_6H_4)OPO_3H$, $(C_6H_4)OSO_3H$, $(C_6H_4)$ $CH_2CO_2H$, and $(C_6H_4)CONH_2$ or a pharmacologically acceptable salt thereof.

2. A method of treating Amyotrophic Lateral Sclerosis in an individual in need of such treatment, comprising the step of administering to the individual a pharmacologically effective dose of a pharmaceutical composition comprising a compound of formula

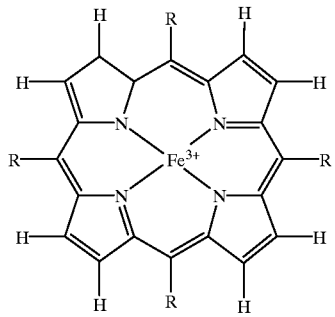

wherein R is $(C_6H_4)CO_2H$, $(C_6H_4)CO_2CH_3$, $(C_6H_4)(3,5-OH)_2$, $(C_6H_4)CH_2OH$, $(C_6H_4)OCH_3$, $(C_6H_4)PO_3H$, $(C_6H_4)SO_3H$, $(C_6H_4)(3-NO_2-4-OH)$, $(C_6H_4)NO_2$, $(C_6H_4)OPO_3H$, $(C_6H_4)OSO_3H$, $(C_6H_4)CH_2CO_2H$, $(C_6H_4)NH_2$, and $(C_6H_4)CONH_2$, or a pharmacologically acceptable salt thereof; and a pharmaceutically acceptable carrier.

3. The method of claim 2, wherein said composition is administered in a dose of from about 0.2 mg/kg to about 5 mg/kg of body weight.

4. The method of claim 2, wherein said composition comprises iron(III) meso 5,10,15,20-tetrakis-(4-carboxyphenyl)porphyrin or a pharmacologically acceptable salt thereof and a pharmaceutically acceptable carrier.

5. The method of claim 2, wherein said composition comprises iron(III) meso 5,10,15,20-tetrakis-(4-carboxymethyl-phenyl)porphyrin or a pharmacologically acceptable salt thereof and a pharmaceutically acceptable carrier.

6. A method of protecting motor neurons from peroxynitrite-mediated oxidative injury in an individual with a neurodegenerative disease involving said peroxynitrite-mediated oxidative injury comprising the step of administering to the individual a pharmacologically effective dose of a pharmaceutical composition comprising a compound of formula

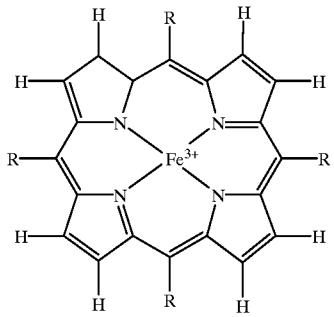

wherein R is $(C_6H_4)CO_2H$, $(C_6H_4)CO_2CH_3$, $(C_6H_4)(3,5-OH)_2$, $(C_6H_4)CH_2OH$, $(C_6H_4)OCH_3$, $(C_6H_4)PO_3H$, $(C_6H_4)SO_3H$, $(C_6H_4)(3-NO_2-4-OH)$, $(C_6H_4)NO_2$, $(C_6H_4)OPO_3H$, $(C_6H_4)OSO_3H$, $(C_6H_4)CH_2CO_2H$, $(C_6H_4)NH_2$, and $(C_6H_4)CONH_2$, or a pharmacologically acceptable salt thereof; and a pharmaceutically acceptable carrier.

7. The method of claim 6, wherein said composition is administered in a dose of from about 0.2 mg/kg to about 5 mg/kg of body weight.

8. The method of claim 6, wherein said composition comprises iron(III) meso 5,10,15,20-tetrakis-(4-carboxyphenyl)porphyrin or a pharmacologically acceptable salt thereof and a pharmaceutically acceptable carrier.

9. The method of claim 6, wherein said pharmaceutical composition comprises iron(III) meso 5,10,15,20-tetrakis-(4-carboxymethyl-phenyl)porphyrin or a pharmacologically acceptable salt thereof and a pharmaceutically acceptable carrier.

10. The method of claim 6, wherein said neurodegenerative disease is selected from the group consisting of Amyotrophic Lateral Sclerosis, Parkinson's Disease and neurodegenerative disease due to MPTP.

11. A method for preserving donor organs comprising the step of immersing said donor organs into a solution, said solution comprising a compound of the formula

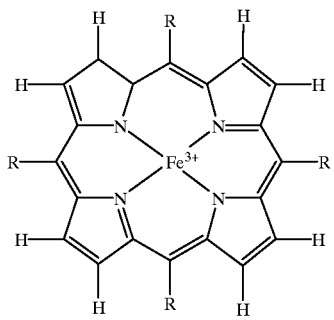

wherein R is $(C_6H_4)CO_2H$, $(C_6H_4)CO_2CH_3$, $(C_6H_4)(3,5-OH)_2$, $(C_6H_4)CH_2OH$, $(C_6H_4)OCH_3$, $(C_6H_4)PO_3H$, $(C_6H_4)SO_3H$, $(C_6H_4)(3-NO_2-4-OH)$, $(C_6H_4)NO_2$, $(C_6H_4)OPO_3H$, $(C_6H_4)OSO_3H$, $(C_6H_4)CH_2CO_2H$, $(C_6H_4)NH_2$, and $(C_6H_4)CONH_2$, or a pharmacologically acceptable salt thereof.

12. The method of claim 11, wherein said compound or a pharmacologically acceptable salt thereof is contained in said solution in a concentration of from about 0.01 $\mu$M to about 10 $\mu$M.

13. The method of claim 12, wherein said compound is iron(III) meso 5,10,15,20-tetrakis-(4-carboxy-phenyl)porphyrin or a pharmacologically acceptable salt thereof.

14. The method of claim 12, wherein said compound is iron(III) meso 5,10,15,20-tetrakis-(4-carboxymethyl-phenyl)porphyrin or a pharmacologically acceptable salt thereof.

* * * * *